(12) United States Patent
Ngai et al.

(10) Patent No.: US 6,410,249 B1
(45) Date of Patent: Jun. 25, 2002

(54) ODORANT RECEPTORS

(75) Inventors: John Ngai; David J. Speca; David M. Lin; Ehud Y. Isacoff; Andrew H. Dittman; Jinhong Fan, all of Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 13 days.

(21) Appl. No.: 09/619,353

(22) Filed: Jul. 19, 2000

Related U.S. Application Data

(60) Provisional application No. 60/144,766, filed on Jul. 20, 1999.

(51) Int. Cl.[7] ................. G01N 33/566; C07K 1/00; C12N 1/20; C12P 21/06; C07H 21/04
(52) U.S. Cl. ............. 435/7.21; 435/6; 435/7.2; 435/69.1; 435/252.3; 436/501; 536/23.5; 530/350
(58) Field of Search .................. 435/6, 69.1, 7.2, 435/7.21, 252.3; 436/501; 536/23.5; 530/350

(56) References Cited

PUBLICATIONS

Bowie et al., 1990, Science 247:1306–1310.*

* cited by examiner

*Primary Examiner*—Yvonne Eyler
*Assistant Examiner*—Michael Brannock
(74) *Attorney, Agent, or Firm*—Richard Aron Osman

(57) ABSTRACT

The invention provides methods and compositions relating to odorant receptors, including a general expression cloning methodology which is useful for identifying novel G protein-coupled receptors and a novel family of odorant receptors and related nucleic acids, ligands, agonists and antagonists. These compositions provide a wide variety of applications such as screening for related receptors, and by modulating the function of the disclosed receptors by modulating their expression or contacting them with agonists, antagonist or ligands modulating reproductive/sexual and non-sexual social behaviors mediated via the olfactory system, reproductive physiologies and olfactory system regulated feeding behaviors, migratory behaviors and events such as conception, implantation, estrous and menstruation.

18 Claims, No Drawings

SEQUENCE LISTING

<160> NUMBER OF SEQ ID NOS: 14

<210> SEQ ID NO 1
<211> LENGTH: 2877
<212> TYPE: DNA
<213> ORGANISM: Carassius auratus
<220> FEATURE:
<221> NAME/KEY: CDS
<222> LOCATION: (34)..(2664)

<400> SEQUENCE: 1

-continued

```
gtcgacccac gcgtccgaca gcctaaagca gtg atg gct ggt ttg gat ttg agc      54
                              Met Ala Gly Leu Asp Leu Ser
                                1               5 ctg gta ctc atg ttg tct gtg ctg gca gga gtc aga gag gtt tca ctg      102
Leu Val Leu Met Leu Ser Val Leu Ala Gly Val Arg Glu Val Ser Leu
        10                  15                  20 aca cag gtt aac caa caa gga gtc ata gcc cct gga gac atc att att      150
Thr Gln Val Asn Gln Gln Gly Val Ile Ala Pro Gly Asp Ile Ile Ile
    25                  30                  35 gga ggt ctt ttt ccc atc cat gag gca gcg gag gca gtg aac ttc act      198
Gly Gly Leu Phe Pro Ile His Glu Ala Ala Glu Ala Val Asn Phe Thr
40                  45                  50                  55 ggc tta aac agc ttc tct tct ttt cag cat cca gtc tgc aac aga tac      246
Gly Leu Asn Ser Phe Ser Ser Phe Gln His Pro Val Cys Asn Arg Tyr
                60                  65                  70 tac aca aaa ggt cta aat cag gct cta gct atg att cat gct gtg gaa      294
Tyr Thr Lys Gly Leu Asn Gln Ala Leu Ala Met Ile His Ala Val Glu
            75                  80                  85 atg gca aac caa tcc ccc atg ttg agc agt ttg aat tta act ctt gga      342
Met Ala Asn Gln Ser Pro Met Leu Ser Ser Leu Asn Leu Thr Leu Gly
        90                  95                 100 tat cgc atc tat gac aca tgt tct gat gtc acg act gca ctt tgg gcc      390
Tyr Arg Ile Tyr Asp Thr Cys Ser Asp Val Thr Thr Ala Leu Trp Ala
    105                 110                 115 gtc caa gat ctc aca cgg ccg tac tcc tac tgt gac tca caa act aac      438
Val Gln Asp Leu Thr Arg Pro Tyr Ser Tyr Cys Asp Ser Gln Thr Asn
120                 125                 130                 135 tct tct caa cct gtc cag cca ata atg gca gta att ggg ccc tct tct      486
Ser Ser Gln Pro Val Gln Pro Ile Met Ala Val Ile Gly Pro Ser Ser
                140                 145                 150 tct gag atc tcc atc gca gtt gcc agg gaa ctc aac ctt ctg atg att      534
Ser Glu Ile Ser Ile Ala Val Ala Arg Glu Leu Asn Leu Leu Met Ile
            155                 160                 165 cca cag ata agt tat gca tct aca gct acg att ctt agt gac aaa agt      582
Pro Gln Ile Ser Tyr Ala Ser Thr Ala Thr Ile Leu Ser Asp Lys Ser
        170                 175                 180 cgt ttt cct gct ttc atg agg act gtc cca aat gat gag tac caa acc      630
Arg Phe Pro Ala Phe Met Arg Thr Val Pro Asn Asp Glu Tyr Gln Thr
    185                 190                 195 cat gcc atg gta caa ctt ctg aag gac aat aaa tgg acc tgg gtt ggg      678
His Ala Met Val Gln Leu Leu Lys Asp Asn Lys Trp Thr Trp Val Gly
200                 205                 210                 215 att atc att aca gat gga gac tat ggg cgt tct gcc atg gaa agt ttt      726
Ile Ile Ile Thr Asp Gly Asp Tyr Gly Arg Ser Ala Met Glu Ser Phe
                220                 225                 230 gtt aag cac act gaa agg gag gga att tgt gtg gcc ttt aag gtg atc      774
Val Lys His Thr Glu Arg Glu Gly Ile Cys Val Ala Phe Lys Val Ile
            235                 240                 245 cta cca gat tca cta gca gac gaa caa aaa tta aac atc cac atc aac      822
Leu Pro Asp Ser Leu Ala Asp Glu Gln Lys Leu Asn Ile His Ile Asn
        250                 255                 260 gag act gtg gac atc att gaa aaa aat act aag gtt aat gtg gtg gtc      870
Glu Thr Val Asp Ile Ile Glu Lys Asn Thr Lys Val Asn Val Val Val
    265                 270                 275 tca ttt gct aag tca tct caa atg aag ttg cta tat gag ggc ctg cgt      918
Ser Phe Ala Lys Ser Ser Gln Met Lys Leu Leu Tyr Glu Gly Leu Arg
280                 285                 290                 295 agt agg aac gtt cca aaa aat aaa gta tgg gtg gcc agc gat aac tgg      966
Ser Arg Asn Val Pro Lys Asn Lys Val Trp Val Ala Ser Asp Asn Trp
```

-continued

|     |     |     | 300 |     |     |     |     | 305 |     |     |     |     | 310 |     |     |      |
|-----|-----|-----|-----|-----|-----|-----|-----|-----|-----|-----|-----|-----|-----|-----|-----|------|
| tct | acc | tct | aaa | aat | att | cta | aaa | gac | gta | aac | ctc | tca | gat | atc | gga | 1014 |
| Ser | Thr | Ser | Lys | Asn | Ile | Leu | Lys | Asp | Val | Asn | Leu | Ser | Asp | Ile | Gly |      |
|     |     |     | 315 |     |     |     |     | 320 |     |     |     |     | 325 |     |     |      |

| aat | ata | ctg | ggc | ttc | acc | ttc | aag | agt | gga | aat | gtt | aca | gct | ttt | ctt | 1062 |
|-----|-----|-----|-----|-----|-----|-----|-----|-----|-----|-----|-----|-----|-----|-----|-----|------|
| Asn | Ile | Leu | Gly | Phe | Thr | Phe | Lys | Ser | Gly | Asn | Val | Thr | Ala | Phe | Leu |      |
|     |     |     | 330 |     |     |     |     | 335 |     |     |     |     | 340 |     |     |      |

| caa | tac | ctt | aag | gat | ctg | aag | ttt | gga | agt | gaa | gct | aag | atg | aac | aat | 1110 |
|-----|-----|-----|-----|-----|-----|-----|-----|-----|-----|-----|-----|-----|-----|-----|-----|------|
| Gln | Tyr | Leu | Lys | Asp | Leu | Lys | Phe | Gly | Ser | Glu | Ala | Lys | Met | Asn | Asn |      |
|     |     |     | 345 |     |     |     |     | 350 |     |     |     |     | 355 |     |     |      |

| tca | ttc | ttg | gaa | gaa | ttt | tta | aaa | ctg | cct | gaa | ata | gga | aat | gct | gca | 1158 |
|-----|-----|-----|-----|-----|-----|-----|-----|-----|-----|-----|-----|-----|-----|-----|-----|------|
| Ser | Phe | Leu | Glu | Glu | Phe | Leu | Lys | Leu | Pro | Glu | Ile | Gly | Asn | Ala | Ala |      |
| 360 |     |     |     |     | 365 |     |     |     |     | 370 |     |     |     |     | 375 |      |

| aac | gct | gta | cag | gaa | cag | att | aaa | aac | aca | cat | ttg | gac | atg | gtc | ttc | 1206 |
|-----|-----|-----|-----|-----|-----|-----|-----|-----|-----|-----|-----|-----|-----|-----|-----|------|
| Asn | Ala | Val | Gln | Glu | Gln | Ile | Lys | Asn | Thr | His | Leu | Asp | Met | Val | Phe |      |
|     |     |     | 380 |     |     |     |     | 385 |     |     |     |     | 390 |     |     |      |

| agt | gtt | cag | atg | gca | gtc | agt | gct | att | gct | aaa | gct | gtg | gtt | gaa | cta | 1254 |
|-----|-----|-----|-----|-----|-----|-----|-----|-----|-----|-----|-----|-----|-----|-----|-----|------|
| Ser | Val | Gln | Met | Ala | Val | Ser | Ala | Ile | Ala | Lys | Ala | Val | Val | Glu | Leu |      |
|     |     |     | 395 |     |     |     |     | 400 |     |     |     |     | 405 |     |     |      |

| tgt | gta | gaa | aga | caa | tgc | aag | acc | cct | tca | gct | atc | caa | ccc | tgg | gag | 1302 |
|-----|-----|-----|-----|-----|-----|-----|-----|-----|-----|-----|-----|-----|-----|-----|-----|------|
| Cys | Val | Glu | Arg | Gln | Cys | Lys | Thr | Pro | Ser | Ala | Ile | Gln | Pro | Trp | Glu |      |
|     |     |     | 410 |     |     |     |     | 415 |     |     |     |     | 420 |     |     |      |

| ctc | tta | aaa | cag | ctg | agg | aac | gtc | act | ttt | gag | aaa | gaa | gga | gtc | atg | 1350 |
|-----|-----|-----|-----|-----|-----|-----|-----|-----|-----|-----|-----|-----|-----|-----|-----|------|
| Leu | Leu | Lys | Gln | Leu | Arg | Asn | Val | Thr | Phe | Glu | Lys | Glu | Gly | Val | Met |      |
|     |     |     | 425 |     |     |     |     | 430 |     |     |     |     | 435 |     |     |      |

| tac | aat | ttt | gac | gcc | aat | gga | gac | att | aat | ttg | ggc | tat | gat | gtc | tgc | 1398 |
|-----|-----|-----|-----|-----|-----|-----|-----|-----|-----|-----|-----|-----|-----|-----|-----|------|
| Tyr | Asn | Phe | Asp | Ala | Asn | Gly | Asp | Ile | Asn | Leu | Gly | Tyr | Asp | Val | Cys |      |
| 440 |     |     |     |     | 445 |     |     |     |     | 450 |     |     |     |     | 455 |      |

| cta | tgg | gat | gac | gat | gaa | tct | gaa | aaa | aat | gac | ata | ata | gca | gaa | tat | 1446 |
|-----|-----|-----|-----|-----|-----|-----|-----|-----|-----|-----|-----|-----|-----|-----|-----|------|
| Leu | Trp | Asp | Asp | Asp | Glu | Ser | Glu | Lys | Asn | Asp | Ile | Ile | Ala | Glu | Tyr |      |
|     |     |     | 460 |     |     |     |     | 465 |     |     |     |     | 470 |     |     |      |

| tat | cca | tct | aac | agc | agt | ttc | act | ttt | aca | agg | aag | aat | cta | agt | aat | 1494 |
|-----|-----|-----|-----|-----|-----|-----|-----|-----|-----|-----|-----|-----|-----|-----|-----|------|
| Tyr | Pro | Ser | Asn | Ser | Ser | Phe | Thr | Phe | Thr | Arg | Lys | Asn | Leu | Ser | Asn |      |
|     |     |     | 475 |     |     |     |     | 480 |     |     |     |     | 485 |     |     |      |

| att | gag | aat | gtg | tta | tct | aag | tgt | tcg | gac | agc | tgt | caa | cca | ggg | gag | 1542 |
|-----|-----|-----|-----|-----|-----|-----|-----|-----|-----|-----|-----|-----|-----|-----|-----|------|
| Ile | Glu | Asn | Val | Leu | Ser | Lys | Cys | Ser | Asp | Ser | Cys | Gln | Pro | Gly | Glu |      |
|     |     |     | 490 |     |     |     |     | 495 |     |     |     |     | 500 |     |     |      |

| tac | aaa | aaa | aca | gca | gag | ggt | cag | cac | act | tgc | tgt | tat | gag | tgt | ctt | 1590 |
|-----|-----|-----|-----|-----|-----|-----|-----|-----|-----|-----|-----|-----|-----|-----|-----|------|
| Tyr | Lys | Lys | Thr | Ala | Glu | Gly | Gln | His | Thr | Cys | Cys | Tyr | Glu | Cys | Leu |      |
|     |     |     | 505 |     |     |     |     | 510 |     |     |     |     | 515 |     |     |      |

| gcc | tgc | gcc | gaa | aac | caa | tac | tcc | aac | cac | aca | gat | gca | gac | aca | tgt | 1638 |
|-----|-----|-----|-----|-----|-----|-----|-----|-----|-----|-----|-----|-----|-----|-----|-----|------|
| Ala | Cys | Ala | Glu | Asn | Gln | Tyr | Ser | Asn | His | Thr | Asp | Ala | Asp | Thr | Cys |      |
| 520 |     |     |     |     | 525 |     |     |     |     | 530 |     |     |     |     | 535 |      |

| tct | aag | tgc | gac | act | gag | agc | ttg | tgg | tca | aac | gct | aat | agc | tca | aaa | 1686 |
|-----|-----|-----|-----|-----|-----|-----|-----|-----|-----|-----|-----|-----|-----|-----|-----|------|
| Ser | Lys | Cys | Asp | Thr | Glu | Ser | Leu | Trp | Ser | Asn | Ala | Asn | Ser | Ser | Lys |      |
|     |     |     | 540 |     |     |     |     | 545 |     |     |     |     | 550 |     |     |      |

| tgt | tat | ccc | aag | ttt | tat | gag | tac | ttt | gag | tgg | aat | agt | ggt | ttt | gcc | 1734 |
|-----|-----|-----|-----|-----|-----|-----|-----|-----|-----|-----|-----|-----|-----|-----|-----|------|
| Cys | Tyr | Pro | Lys | Phe | Tyr | Glu | Tyr | Phe | Glu | Trp | Asn | Ser | Gly | Phe | Ala |      |
|     |     |     | 555 |     |     |     |     | 560 |     |     |     |     | 565 |     |     |      |

| atc | gcc | ctg | ctg | acg | ctg | gct | gcc | ctc | ggc | atc | cta | ctc | ctc | atc | tca | 1782 |
|-----|-----|-----|-----|-----|-----|-----|-----|-----|-----|-----|-----|-----|-----|-----|-----|------|
| Ile | Ala | Leu | Leu | Thr | Leu | Ala | Ala | Leu | Gly | Ile | Leu | Leu | Leu | Ile | Ser |      |
|     |     |     | 570 |     |     |     |     | 575 |     |     |     |     | 580 |     |     |      |

| atg | tcc | gca | ctg | ttc | ttc | tgg | caa | agg | aac | tct | cta | gtg | gtt | aaa | gct | 1830 |
|-----|-----|-----|-----|-----|-----|-----|-----|-----|-----|-----|-----|-----|-----|-----|-----|------|
| Met | Ser | Ala | Leu | Phe | Phe | Trp | Gln | Arg | Asn | Ser | Leu | Val | Val | Lys | Ala |      |
|     |     |     | 585 |     |     |     |     | 590 |     |     |     |     | 595 |     |     |      |

| gca | ggt | gga | cca | ctt | tgt | cat | ctg | atc | ctt | ttc | tcc | ctg | ctg | ggc | agt | 1878 |
|-----|-----|-----|-----|-----|-----|-----|-----|-----|-----|-----|-----|-----|-----|-----|-----|------|
| Ala | Gly | Gly | Pro | Leu | Cys | His | Leu | Ile | Leu | Phe | Ser | Leu | Leu | Gly | Ser |      |
| 600 |     |     |     |     | 605 |     |     |     |     | 610 |     |     |     |     | 615 |      |

| ttt | atc | agt | gtc | att | ttc | ttt | gtg | ggt | gaa | ccg | agc | aat | gag | tcc | tgt | 1926 |

| | | |
|---|---|---|
| Phe Ile Ser Val Ile Phe Phe Val Gly Glu Pro Ser Asn Glu Ser Cys<br>620                          625                    630 | | |
| agg gta agg cag gtc atc ttt ggc ctg agc ttc acg ctg tgt gtt tca<br>Arg Val Arg Gln Val Ile Phe Gly Leu Ser Phe Thr Leu Cys Val Ser<br>           635                       640                       645 | 1974 |
| tgc atc tta gtg aag tcc ttg aag atc ctt ctg gcg ttc cag atg aac<br>Cys Ile Leu Val Lys Ser Leu Lys Ile Leu Leu Ala Phe Gln Met Asn<br>650                          655                          660 | 2022 |
| cta gag ctg aag gag ctt ctt cgt aaa ctc tac aag ccg tat gtg atc<br>Leu Glu Leu Lys Glu Leu Leu Arg Lys Leu Tyr Lys Pro Tyr Val Ile<br>        665                       670                       675 | 2070 |
| gtt tgc atg tgt atg ggg ctt cag gtc acc att tgc act ctt tgg ctg<br>Val Cys Met Cys Met Gly Leu Gln Val Thr Ile Cys Thr Leu Trp Leu<br>680                          685                       690                   695 | 2118 |
| acc ttg cac agg cct ttt att gaa aaa gtg gtg caa ccc aaa tcc att<br>Thr Leu His Arg Pro Phe Ile Glu Lys Val Val Gln Pro Lys Ser Ile<br>                 700                       705                     710 | 2166 |
| ctc ctg gaa tgc aat gag ggt tca gat ttg atg ttt ggg tta atg ctg<br>Leu Leu Glu Cys Asn Glu Gly Ser Asp Leu Met Phe Gly Leu Met Leu<br>715                          720                          725 | 2214 |
| ggt tac ata gtt ttg ctg gcg ctg ata tgt ttc act ttt gct tat aaa<br>Gly Tyr Ile Val Leu Leu Ala Leu Ile Cys Phe Thr Phe Ala Tyr Lys<br>           730                       735                       740 | 2262 |
| ggc agg aaa ctt ccg cag aag tat aac gaa gca aag ttc atc aca ttt<br>Gly Arg Lys Leu Pro Gln Lys Tyr Asn Glu Ala Lys Phe Ile Thr Phe<br>745                          750                          755 | 2310 |
| ggt atg ctc atc tac ctc atg gcc tgg gtc att ttt atc cca gtg cac<br>Gly Met Leu Ile Tyr Leu Met Ala Trp Val Ile Phe Ile Pro Val His<br>760                          765                       770                   775 | 2358 |
| gtg acc acc agt ggc aaa tat gta ccg gct gtg gag gta gtt gtt att<br>Val Thr Thr Ser Gly Lys Tyr Val Pro Ala Val Glu Val Val Val Ile<br>                 780                       785                     790 | 2406 |
| ctc att tca aac tat ggg atc ctg agc tgc cac ttt ttg cca aaa tgt<br>Leu Ile Ser Asn Tyr Gly Ile Leu Ser Cys His Phe Leu Pro Lys Cys<br>795                          800                        805 | 2454 |
| tac ata att att ttt aaa aag gag tat aat acc aaa gat gca ttc ttg<br>Tyr Ile Ile Ile Phe Lys Lys Glu Tyr Asn Thr Lys Asp Ala Phe Leu<br>        810                       815                     820 | 2502 |
| aaa aat gtt ttt gaa tac gcc aga aag agc tct gag aac atc agg ggc<br>Lys Asn Val Phe Glu Tyr Ala Arg Lys Ser Ser Glu Asn Ile Arg Gly<br>825                          830                        835 | 2550 |
| ttg tct gga act gat cca cac agt aaa act gac aat tca gtc tat gtc<br>Leu Ser Gly Thr Asp Pro His Ser Lys Thr Asp Asn Ser Val Tyr Val<br>840                          845                        850                   855 | 2598 |
| ata tcc aac ccg tca ctt gtg cct gag gag aaa caa gtt tct gta cca<br>Ile Ser Asn Pro Ser Leu Val Pro Glu Glu Lys Gln Val Ser Val Pro<br>                 860                       865                     870 | 2646 |
| gaa ata gac aat gtg ctt taaagtagtt gcaagaattt gagatcacga<br>Glu Ile Asp Asn Val Leu<br>                 875 | 2694 |
| gtcaaagcaa ccattcagac aaatttggt cttcatttga catgaaactt gtatttcaca | 2754 |
| taatgatctt taaaatacc aaacttcatg atgatcattt taattatga atactttcat | 2814 |
| ttgtggaaaa caaataaaat gtgtatattt gtgtatattt gaaattaaaa aaaaaaaaa | 2874 |
| aaa | 2877 |

<210> SEQ ID NO 2
<211> LENGTH: 877
<212> TYPE: PRT

-continued

```
<213> ORGANISM: Carassius auratus

<400> SEQUENCE: 2

Met Ala Gly Leu Asp Leu Ser Leu Val Leu Met Leu Ser Val Leu Ala
 1               5                  10                  15

Gly Val Arg Glu Val Ser Leu Thr Gln Val Asn Gln Gln Gly Val Ile
             20                  25                  30

Ala Pro Gly Asp Ile Ile Gly Gly Leu Phe Pro Ile His Glu Ala
         35                  40                  45

Ala Glu Ala Val Asn Phe Thr Gly Leu Asn Ser Phe Ser Ser Phe Gln
     50                  55                  60

His Pro Val Cys Asn Arg Tyr Tyr Thr Lys Gly Leu Asn Gln Ala Leu
 65                  70                  75                  80

Ala Met Ile His Ala Val Glu Met Ala Asn Gln Ser Pro Met Leu Ser
                 85                  90                  95

Ser Leu Asn Leu Thr Leu Gly Tyr Arg Ile Tyr Asp Thr Cys Ser Asp
            100                 105                 110

Val Thr Thr Ala Leu Trp Ala Val Gln Asp Leu Thr Arg Pro Tyr Ser
        115                 120                 125

Tyr Cys Asp Ser Gln Thr Asn Ser Ser Gln Pro Val Gln Pro Ile Met
    130                 135                 140

Ala Val Ile Gly Pro Ser Ser Glu Ile Ser Ile Ala Val Ala Arg
145                 150                 155                 160

Glu Leu Asn Leu Leu Met Ile Pro Gln Ile Ser Tyr Ala Ser Thr Ala
                165                 170                 175

Thr Ile Leu Ser Asp Lys Ser Arg Phe Pro Ala Phe Met Arg Thr Val
            180                 185                 190

Pro Asn Asp Glu Tyr Gln Thr His Ala Met Val Gln Leu Leu Lys Asp
        195                 200                 205

Asn Lys Trp Thr Trp Val Gly Ile Ile Ile Thr Asp Gly Asp Tyr Gly
210                 215                 220

Arg Ser Ala Met Glu Ser Phe Val Lys His Thr Glu Arg Glu Gly Ile
225                 230                 235                 240

Cys Val Ala Phe Lys Val Ile Leu Pro Asp Ser Leu Ala Asp Glu Gln
                245                 250                 255

Lys Leu Asn Ile His Ile Asn Glu Thr Val Asp Ile Ile Glu Lys Asn
            260                 265                 270

Thr Lys Val Asn Val Val Ser Phe Ala Lys Ser Ser Gln Met Lys
        275                 280                 285

Leu Leu Tyr Glu Gly Leu Arg Ser Arg Asn Val Pro Lys Asn Lys Val
    290                 295                 300

Trp Val Ala Ser Asp Asn Trp Ser Thr Ser Lys Asn Ile Leu Lys Asp
305                 310                 315                 320

Val Asn Leu Ser Asp Ile Gly Asn Ile Leu Gly Phe Thr Phe Lys Ser
                325                 330                 335

Gly Asn Val Thr Ala Phe Leu Gln Tyr Leu Lys Asp Leu Lys Phe Gly
            340                 345                 350

Ser Glu Ala Lys Met Asn Asn Ser Phe Leu Glu Glu Phe Leu Lys Leu
        355                 360                 365

Pro Glu Ile Gly Asn Ala Ala Asn Ala Val Gln Glu Gln Ile Lys Asn
    370                 375                 380

Thr His Leu Asp Met Val Phe Ser Val Gln Met Ala Val Ser Ala Ile
385                 390                 395                 400
```

-continued

```
Ala Lys Ala Val Val Glu Leu Cys Val Glu Arg Gln Cys Lys Thr Pro
            405                 410                 415
Ser Ala Ile Gln Pro Trp Glu Leu Leu Lys Gln Leu Arg Asn Val Thr
            420                 425                 430
Phe Glu Lys Glu Gly Val Met Tyr Asn Phe Asp Ala Asn Gly Asp Ile
            435                 440                 445
Asn Leu Gly Tyr Asp Val Cys Leu Trp Asp Asp Glu Ser Glu Lys
        450                 455                 460
Asn Asp Ile Ile Ala Glu Tyr Tyr Pro Ser Asn Ser Ser Phe Thr Phe
465                 470                 475                 480
Thr Arg Lys Asn Leu Ser Asn Ile Glu Asn Val Leu Ser Lys Cys Ser
            485                 490                 495
Asp Ser Cys Gln Pro Gly Glu Tyr Lys Lys Thr Ala Glu Gly Gln His
            500                 505                 510
Thr Cys Cys Tyr Glu Cys Leu Ala Cys Ala Glu Asn Gln Tyr Ser Asn
            515                 520                 525
His Thr Asp Ala Asp Thr Cys Ser Lys Cys Asp Thr Glu Ser Leu Trp
        530                 535                 540
Ser Asn Ala Asn Ser Ser Lys Cys Tyr Pro Lys Phe Glu Tyr Phe
545                 550                 555                 560
Glu Trp Asn Ser Gly Phe Ala Ile Ala Leu Leu Thr Leu Ala Ala Leu
            565                 570                 575
Gly Ile Leu Leu Leu Ile Ser Met Ser Ala Leu Phe Phe Trp Gln Arg
            580                 585                 590
Asn Ser Leu Val Val Lys Ala Ala Gly Gly Pro Leu Cys His Leu Ile
            595                 600                 605
Leu Phe Ser Leu Leu Gly Ser Phe Ile Ser Val Ile Phe Phe Val Gly
        610                 615                 620
Glu Pro Ser Asn Glu Ser Cys Arg Val Arg Gln Val Ile Phe Gly Leu
625                 630                 635                 640
Ser Phe Thr Leu Cys Val Ser Cys Ile Leu Val Lys Ser Leu Lys Ile
            645                 650                 655
Leu Leu Ala Phe Gln Met Asn Leu Glu Leu Lys Glu Leu Leu Arg Lys
            660                 665                 670
Leu Tyr Lys Pro Tyr Val Ile Val Cys Met Cys Met Gly Leu Gln Val
            675                 680                 685
Thr Ile Cys Thr Leu Trp Leu Thr Leu His Arg Pro Phe Ile Glu Lys
        690                 695                 700
Val Val Gln Pro Lys Ser Ile Leu Leu Glu Cys Asn Glu Gly Ser Asp
705                 710                 715                 720
Leu Met Phe Gly Leu Met Leu Gly Tyr Ile Val Leu Leu Ala Leu Ile
            725                 730                 735
Cys Phe Thr Phe Ala Tyr Lys Gly Arg Lys Leu Pro Gln Lys Tyr Asn
            740                 745                 750
Glu Ala Lys Phe Ile Thr Phe Gly Met Leu Ile Tyr Leu Met Ala Trp
            755                 760                 765
Val Ile Phe Ile Pro Val His Val Thr Thr Ser Gly Lys Tyr Val Pro
        770                 775                 780
Ala Val Glu Val Val Ile Leu Ile Ser Asn Tyr Gly Ile Leu Ser
785                 790                 795                 800
Cys His Phe Leu Pro Lys Cys Tyr Ile Ile Phe Lys Lys Glu Tyr
            805                 810                 815
Asn Thr Lys Asp Ala Phe Leu Lys Asn Val Phe Glu Tyr Ala Arg Lys
```

```
                    820                 825                 830
Ser Ser Glu Asn Ile Arg Gly Leu Ser Gly Thr Asp Pro His Ser Lys
        835                 840                 845

Thr Asp Asn Ser Val Tyr Val Ile Ser Asn Pro Ser Leu Val Pro Glu
    850                 855                 860

Glu Lys Gln Val Ser Val Pro Glu Ile Asp Asn Val Leu
865             870                 875
```

<210> SEQ ID NO 3
<211> LENGTH: 315
<212> TYPE: PRT
<213> ORGANISM: Carassius auratus

<400> SEQUENCE: 3

```
Thr Val Arg Ser Arg Asn Asp Tyr Gly Asn Gly Ile Ala Ala Phe
1               5                   10                  15

Glu Glu Ala Ala Lys Glu Gly Val Cys Ile Glu Tyr Ser Glu Ala
                20                  25                  30

Ile Leu Asn Asn Asp Pro Gln Glu Gln Phe Leu Lys Thr Leu Glu Val
            35                  40                  45

Ile Lys Lys Gly Thr Ala Arg Val Val Leu Ala Phe Ile Ala Leu Gly
    50                  55                  60

Asp Phe Leu Pro Leu Leu Lys Val Ile Leu Gln His Asn Ile Thr Gly
65                  70                  75                  80

Ile Gln Trp Val Gly Ser Glu Ser Trp Ile Thr Ser Gln Thr Leu Ala
                85                  90                  95

Glu Thr Lys Glu Tyr Ser Phe Leu Ser Gly Ala Val Gly Phe Ala Ile
            100                 105                 110

Ala Asn Ala Lys Ile Met Gly Leu Arg Glu Phe Leu Val Asn Val His
        115                 120                 125

Pro Tyr Lys Glu Pro Lys Asn Glu Leu Leu Lys Glu Phe Trp Glu Ile
    130                 135                 140

Val Phe Gln Cys Ser Phe Asn Ser Ile Gly Ser Gly Cys Thr Gly Ser
145                 150                 155                 160

Glu Arg Leu Ala Glu Leu Gln Asn Glu Tyr Thr Asp Val Ser Glu Leu
                165                 170                 175

Arg Ile Ala Asn Lys Val Tyr Thr Ala Val Tyr Ala Ile Ala Tyr Thr
            180                 185                 190

Leu His Asn Ile Leu Lys Glu Phe Arg Thr Ser Thr Asn Ser Ser Lys
        195                 200                 205

Ile Gly Trp Pro Ile Pro Gln Met Val Leu Lys Tyr Met Arg Asp Val
    210                 215                 220

Arg Phe Thr Val Lys Thr Gly Glu Glu Ile Phe Phe Asp Glu Ser Gly
225                 230                 235                 240

Asp Pro Val Ala Arg Tyr Asp Leu Val Asn Trp Gln Ser Ala Glu Asp
                245                 250                 255

Gly Ser Met Arg Phe Glu Leu Val Gly Leu Tyr Asp Ser Ser Leu Pro
            260                 265                 270

Ser Glu His Leu Gln Val Asn Gln Glu His Ile Leu Trp Ala Glu Lys
        275                 280                 285

Ser Gly Gln Leu Pro Val Ser Val Cys Ser Glu Ile Cys Pro Pro Gly
    290                 295                 300

Thr Arg Lys Ala Val Gln Lys Gly Arg Pro Val
305                 310                 315
```

<210> SEQ ID NO 4
<211> LENGTH: 323
<212> TYPE: PRT
<213> ORGANISM: Carassius auratus

<400> SEQUENCE: 4

Ala Leu Ser Asn Asp Asn Asp Tyr Gly Lys Asn Gly Ile Ala Thr Phe
  1               5                  10                  15

Ile Lys Ala Ala Gln Glu Glu Gly Val Cys Ile Glu Tyr Ser Gln Ala
                 20                  25                  30

Phe Glu Ser Thr Gly Ser Lys Thr Ser Leu Lys Asn Ile Val Asp Thr
             35                  40                  45

Ile Arg Thr Ser Thr Ser Lys Val Ile Met Ala Phe Met Ser His Arg
 50                  55                  60

Glu Ile Lys Ile Leu Val Asp Glu Leu Tyr Arg Gln Asn Ile Thr Gly
 65                  70                  75                  80

Leu Gln Trp Ile Gly Ser Asp Ala Trp Ile Thr Asp Asp Ser Leu Ala
                 85                  90                  95

Asp Ser Gln Gly Asn Thr Leu Leu Ile Gly Ser Ile Gly Phe Thr Val
            100                 105                 110

Arg Asn Ala Lys Ile Pro Gly Leu Gly Pro Phe Leu Gln Lys Leu Asn
            115                 120                 125

Pro Ser Gln Phe Pro Lys Ser Met Phe Leu Lys Glu Phe Trp Glu Ser
130                 135                 140

Ile Phe Gln Cys Ser Leu Ser Pro Asn Ala Leu Gln Arg Ala Cys Asn
145                 150                 155                 160

Gly Ser Glu His Leu Lys Tyr Val Lys His Pro Phe Thr Asp Val Ser
                165                 170                 175

Asp Leu Arg Tyr Val Asn Asn Val Tyr Asn Ala Val Tyr Ala Ile Ala
            180                 185                 190

His Ala Leu His Asn Leu Leu Ser Cys Asn His Gln Lys Gly Pro Phe
            195                 200                 205

Ala Asn Val Thr Cys Ala Gln Pro Thr Ile Ile Gln Pro Trp Gln Ile
210                 215                 220

Leu His Tyr Met Gln Thr Val Asn Phe Thr Met Asn Gly Gly Glu Ser
225                 230                 235                 240

Val Phe Phe Asp Ser Lys Gly Asp Ser Pro Ala Arg Tyr Glu Leu Val
                245                 250                 255

Asn Leu Gln Asn Ile Thr Lys Gly Thr Met Glu Val Val Thr Ile Gly
            260                 265                 270

Tyr Tyr Asp Ala Ile Gln Pro Arg Gly Gln Gln Phe Thr Met Asn Asn
            275                 280                 285

Val Asn Ile Thr Trp Gly Gly Leu Arg Thr Val Pro Val Ser Val
            290                 295                 300

Cys Ser Glu Ser Cys Pro Leu Gly Thr Arg Lys Ala Val Gln Lys Gly
305                 310                 315                 320

Arg Pro Ile

<210> SEQ ID NO 5
<211> LENGTH: 300
<212> TYPE: PRT
<213> ORGANISM: Carassius auratus

<400> SEQUENCE: 5

Ala Val Asn Ser Asp Asn Asp Tyr Gly Asn Asn Gly Met Ala Ile Phe

```
             1               5                  10                 15
           Leu Lys Thr Ala Thr Glu Glu Gly Ile Cys Val Glu Tyr Ser Val Lys
                           20                  25                 30

Phe Leu Arg Thr Glu His Glu Lys Ile Arg Asn Val Val Asp Ile Ile
                           35                  40                 45

Lys Gln Gly Thr Thr Lys Val Ile Val Ala Phe Leu Thr Gly Phe Glu
                           50                  55                 60

Met Lys Ser Leu Ile Glu Gln Leu Gly Ile Gln Asn Ile Thr Gly Leu
            65                  70                 75                  80

Gln Met Ile Gly Val Glu Ala Trp Ile Thr Ser Lys Ser Leu Met Thr
                               85                 90                 95

Pro Asn Ser Phe His Val Leu Gly Gly Ser Leu Gly Phe Ala Val Arg
                           100                 105                110

Lys Ile Gln Ile Glu Gly Phe Ala Asp Tyr Val Met Lys Ala Phe Trp
                           115                 120                125

Asp Thr Ala Phe Pro Cys Ser Phe Asn Ala Lys Leu Asn Cys Ser Arg
                           130                 135                140

Tyr Gln Asp Leu Ser Val Val Lys Asn Tyr Asn Asp Val Pro Glu
           145                 150                 155                160

Gln Arg Phe Leu Ser Tyr Val Tyr Lys Ala Val Tyr Ala Val Ala His
                           165                 170                175

Ser Leu His Ser Leu Leu Lys Cys Arg Glu Arg Asp Gly Cys Glu Glu
                           180                 185                190

Gly Leu Thr Ile Gln Pro Gln Met Val Glu Ala Leu Lys Lys Val
                           195                 200                205

Asn Phe Thr Leu Lys Thr Gly Asp His Val Trp Phe Asp Ser Thr Gly
                210                 215                 220

Gly Ala Val Ala Gln Tyr Glu Ile Val Asn Trp Gln Gln Asp Ser Asp
           225                 230                 235                240

Gly Ser Phe Arg Phe Lys Ser Val Gly Tyr Tyr Asp Ala Ser Leu Pro
                           245                 250                255

Pro Asp Gln Arg Phe Val Ile Ile Thr Lys Asn Ile Ile Trp Ala Arg
                           260                 265                270

Gly Gln Leu Glu Lys Pro Arg Ser Val Cys Ser Glu Ser Cys Pro Pro
                           275                 280                285

Gly Thr Arg Lys Ala Ala Gln Lys Gly Arg Pro Val
                           290                 295                300

<210> SEQ ID NO 6
<211> LENGTH: 323
<212> TYPE: PRT
<213> ORGANISM: Carassius auratus

<400> SEQUENCE: 6

Cys Ile Ala Ala Glu Asp Asp Tyr Gly Lys Tyr Gly Ile Lys Arg Phe
            1               5                  10                 15

Lys Glu Val Val Glu Glu Ala Gly Val Cys Ile Ser Phe Ser Glu Thr
                           20                  25                 30

Leu Pro Lys Val Ser Asn Pro Glu Ala Ile Glu Arg Ile Val Gln Thr
                           35                  40                 45

Val Pro Asp Ser Thr Ala Lys Ile Ile Val Val Phe Ser Ser Asp Val
                           50                  55                 60

Asp Met Ser Pro Leu Val Gly Glu Leu Leu Arg Asn Asn Val Thr Asn
            65                  70                 75                  80
```

-continued

```
Arg Thr Trp Ile Ala Ser Glu Ala Trp Val Thr Ser Ala Ala Ile Ser
                 85                  90                  95

Arg His Pro Asp Ile Leu Pro Val Leu Gly Thr Ile Gly Phe Ala
            100                 105                 110

Val Lys Arg Ala Glu Ile Pro Gly Leu Lys Glu His Leu Leu Ser Val
            115                 120                 125

Thr Pro Tyr Asn Asp Thr Leu Thr Glu Glu Phe Trp Gly Ile Val Phe
        130                 135                 140

Asn Cys Thr Leu Asn Tyr Arg Gln Val Leu Arg Gly Thr Arg Arg Cys
145                 150                 155                 160

Thr Gly Glu Glu Met Leu Glu Lys Leu Asn Asn Thr Phe Thr Asp Val
                165                 170                 175

Ser Gln Leu Arg Ile Thr Tyr Asn Val Tyr Lys Ala Val Tyr Ala Val
            180                 185                 190

Ala His Ala Leu His Asn Leu Glu His Cys Lys Pro Gly Ser Gly Pro
        195                 200                 205

Phe Glu Asn Gly Thr Cys Ala Asp Ile Thr Lys Phe Glu Pro Trp Gln
        210                 215                 220

Leu Met Tyr Tyr Leu Lys Asn Leu Arg Tyr Thr Val Pro His Thr Lys
225                 230                 235                 240

Glu Glu Ile Tyr Phe His Asp Gly Asp Val Asp Gly Phe Tyr Glu Ile
                245                 250                 255

Leu Asn Trp Gln Ser Asp Ser Glu Gly Gly Ile Ala Tyr Thr Pro Ile
            260                 265                 270

Gly Tyr Tyr Asn Ser Thr Ala Ala Pro Glu Glu Arg Leu Ile Ile Asn
        275                 280                 285

Asn Gly Ser Ile Ile Trp Asn Asn Asp Ile Leu Glu Thr Pro Arg Ser
290                 295                 300

Val Cys Ser Glu Arg Cys Gln Pro Gly Thr Arg Met Gly Ile Arg Gln
305                 310                 315                 320

Gly Glu Pro

<210> SEQ ID NO 7
<211> LENGTH: 835
<212> TYPE: PRT
<213> ORGANISM: Carassius auratus

<400> SEQUENCE: 7

Met Leu Leu Phe Leu Tyr Thr Leu Thr Leu Phe Asn His Phe His Thr
  1               5                  10                  15

Lys Ala Glu Lys Ile Leu Cys Gln Met Met Gly Asp Ala Lys Tyr Pro
             20                  25                  30

Leu Leu Ser Lys Asp Gly Glu Ala Thr Ile Gly Gly Ile Phe Ala Met
         35                  40                  45

His Ser Lys Glu Thr Leu Pro Ser Phe Glu Phe Thr Gln Lys Pro Gln
     50                  55                  60

Pro Leu Leu Cys Ser Ser Val Asn Leu Pro Asp Phe Arg Leu Ala Gln
 65                  70                  75                  80

Ile Met Ile Phe Ala Ile Glu Glu Ile Asn Arg Ser Gln Met Leu Leu
                 85                  90                  95

Pro Asn Val Ser Ile Gly Tyr Gln Ile Tyr Asp Thr Cys Ser Ser Arg
            100                 105                 110

Met Ser Ser Met Ser Ala Thr Met Gly Leu Met Asn Gly Pro Glu Phe
        115                 120                 125
```

-continued

```
Ala Ala Gly Glu Thr Cys Asn Gly Glu Ser Ser Ile His Ala Ile Ile
        130                 135                 140

Gly Glu Thr Glu Ser Ser Ala Thr Val Ile Leu Ser Arg Thr Thr Gly
145                 150                 155                 160

Pro Phe Lys Ile Pro Val Ile Ser His Thr Ala Ser Cys Glu Cys Leu
                165                 170                 175

Ser Asn Arg Lys Asp His Pro Ser Phe Phe Arg Thr Ile Ser Ser Asp
                180                 185                 190

Tyr His Gln Ser Arg Ala Leu Ala Tyr Ile Val Lys His Leu Gly Trp
            195                 200                 205

Ser Trp Val Gly Thr Val Asn Ser Asp Asn Asp Tyr Gly Asn Tyr Gly
    210                 215                 220

Met Ala Ile Phe Leu Asn Thr Ala Gln Lys Glu Gly Ile Cys Val Glu
225                 230                 235                 240

Tyr Ser Glu Arg Phe Tyr Arg Thr Glu Pro Glu Lys Leu Lys Lys Val
                245                 250                 255

Val Asp Thr Ile Lys Lys Gly Thr Ala Lys Val Ile Val Ala Phe Val
                260                 265                 270

Ser Phe Ile Glu Met Gly Leu Leu Ile Asp Gln Leu Asn Thr Leu Asn
            275                 280                 285

Ile Thr Gly Leu Gln Ile Ile Gly Val Glu Gly Trp Ile Thr Ser Lys
    290                 295                 300

Ser Leu Ile Thr Pro Lys Ser Phe Gln Val Met Gly Gly Ser Leu Gly
305                 310                 315                 320

Phe Ala Leu Arg Lys Ile Asn Leu Glu Gly Phe Ser Asp Tyr Val Val
                325                 330                 335

Lys Xaa Phe Trp Asp Thr Ala Phe Pro Cys Ser Gln Ile Lys Gly Asn
                340                 345                 350

Ile Ser Gln His Glu Ile Asn Cys Xaa Lys Tyr Gln Asp Leu Leu Ala
            355                 360                 365

Leu Lys Lys Tyr Asn Glu Asp Val Pro Glu Xaa Xaa Tyr Ser Ser His
    370                 375                 380

Val Tyr Lys Ala Val Tyr Ala Val Ala His Ser Leu His Ser Leu Leu
385                 390                 395                 400

Lys Cys Lys Glu Gln Xaa Gly Cys Glu Lys Asp Leu Thr Ile Gln Pro
                405                 410                 415

Gln Gln Val Val Glu Ala Leu Lys Lys Val Asn Phe Thr Val Lys Phe
                420                 425                 430

Gly Asp Arg Val Trp Phe Asp Arg Thr Gly Ala Ala Val Ala Gln Tyr
            435                 440                 445

Glu Val Val Asn Trp Gln Gln Asp Ser Asp Gly Ser Leu His Phe Lys
    450                 455                 460

Ser Val Gly Tyr Tyr Asp Ala Ser Leu Pro Pro Asp Gln Gln Phe Val
465                 470                 475                 480

Leu Lys Thr Glu Asn Ile Ile Trp Ala Lys Gly Gln Leu Glu Lys Pro
                485                 490                 495

Asn Ser Val Cys Ser Glu Ser Cys Leu Pro Gly Thr Arg Lys Ala Ala
                500                 505                 510

Gln Lys Gly Arg Pro Val Cys Cys Tyr Asp Cys Ile Pro Cys Ala Glu
            515                 520                 525

Gly Glu Ile Ser Asn Glu Thr Asp Ser Asn Asn Cys Lys Gln Cys Pro
    530                 535                 540

Arg Glu Tyr Trp Ser Asn Ala Glu Lys Thr Lys Cys Val Leu Lys Ala
```

```
                545                 550                 555                 560
Val Glu Phe Leu Ser Phe Thr Glu Val Met Gly Ile Val Leu Ala Phe
                565                 570                 575

Phe Ser Leu Phe Gly Ala Gly Leu Thr Ala Leu Val Ala Ile Leu Phe
                580                 585                 590

Tyr Arg Met Arg Asp Thr Pro Ile Val Lys Ala Asn Asn Ser Glu Leu
                595                 600                 605

Ser Phe Leu Leu Leu Phe Ser Leu Thr Leu Cys Phe Leu Cys Ser Leu
                610                 615                 620

Thr Phe Ile Gly Gln Pro Asn Glu Trp Ser Cys Met Leu Arg His Thr
625                 630                 635                 640

Ala Phe Gly Ile Thr Phe Val Leu Cys Ile Ser Cys Val Leu Gly Lys
                645                 650                 655

Thr Ile Val Val Leu Met Ala Phe Lys Ala Thr Leu Pro Gly Ser Asn
                660                 665                 670

Val Met Lys Trp Phe Gly Pro Ala Gln Gln Arg Leu Ser Val Leu Ala
                675                 680                 685

Leu Thr Phe Ile Gln Ile Leu Ile Cys Val Leu Trp Leu Thr Ile Ser
                690                 695                 700

Pro Pro Phe Pro Tyr Lys Asn Met Lys Tyr Phe Lys Glu Lys Ile Ile
705                 710                 715                 720

Leu Glu Cys Ser Leu Gly Ser Ser Ile Ser Phe Trp Ala Val Leu Gly
                725                 730                 735

Tyr Ile Gly Leu Leu Ala Val Leu Cys Phe Ile Leu Ala Phe Leu Ala
                740                 745                 750

Arg Thr Leu Pro Asp Asn Phe Asn Glu Ala Lys Phe Ile Thr Phe Ser
                755                 760                 765

Met Leu Ile Phe Cys Ala Val Trp Ile Thr Phe Ile Pro Ala Tyr Val
                770                 775                 780

Ser Ser Pro Gly Lys Tyr Thr Val Ala Val Glu Ile Phe Ala Ile Leu
785                 790                 795                 800

Ala Ser Ser Phe Gly Leu Leu Phe Cys Ile Phe Ala Pro Lys Cys Tyr
                805                 810                 815

Ile Ile Leu Leu Lys Pro Asp Gln Asn Thr Lys Lys His Met Met Gly
                820                 825                 830

Lys Thr Phe
        835

<210> SEQ ID NO 8
<211> LENGTH: 856
<212> TYPE: PRT
<213> ORGANISM: Carassius auratus

<400> SEQUENCE: 8

Met Ala Lys Arg Thr Ile Pro Leu Val Leu Leu Leu Val Val Val Tyr
1               5                   10                  15

Gly Val Cys Val Pro Ala Ser Ala Gln Val Cys Arg Leu Leu Gly Leu
                20                  25                  30

Pro Ala Leu Pro Leu Leu Ser Ala His Lys Asp Ile Asn Ile Gly Ala
            35                  40                  45

Ile Phe Ser Phe His Arg Ser Ala Leu Leu Lys Met His Pro Phe Thr
        50                  55                  60

Ser Lys Pro Glu Pro Thr Thr Cys Ile Ser Phe Asn Leu Arg Glu Phe
65                  70                  75                  80
```

```
Lys Phe Ala Gln Thr Leu Ile Phe Ala Ile Glu Glu Ile Asn Asn Ser
                85                  90                  95

Thr Gln Leu Leu Pro Gly Val Ser Leu Gly Tyr Lys Ile Tyr Asp Ser
            100                 105                 110

Cys Ser Ser Val Ala Leu Thr Val Leu Ser Gly Met Ala Leu Met Asn
            115                 120                 125

Gly Tyr Glu Glu Thr Leu Ser Asp Thr Ser Cys Ser Arg Pro Pro Ala
            130                 135                 140

Val His Ala Ile Val Gly Glu Ser Asn Ser Ser Pro Thr Ile Gly Leu
145                 150                 155                 160

Ala Ser Leu Val Gly Pro Phe Ser Leu Pro Val Ile Ser His Phe Ala
                165                 170                 175

Thr Cys Ala Cys Leu Ser Asn Arg Lys Met Tyr Pro Ser Phe Phe Arg
            180                 185                 190

Thr Ile Pro Ser Asp Tyr Tyr Gln Ser Arg Ala Leu Ala Lys Leu Val
            195                 200                 205

Lys His Phe Gly Trp Thr Trp Val Gly Thr Val Arg Ser Arg Ser Asp
            210                 215                 220

Tyr Gly Ser Asn Gly Ile Ala Ala Phe Glu Glu Ser Ala Lys Glu Glu
225                 230                 235                 240

Gly Ile Cys Ile Glu Tyr Ser Glu Ala Ile Phe Lys Thr Asp Pro Gln
                245                 250                 255

Asp Gln Phe Leu Lys Thr Val Glu Val Ile Lys Lys Gly Thr Ala Arg
            260                 265                 270

Val Val Leu Ala Phe Ile Ala Leu Gly Asp Phe Val Pro Leu Leu Lys
            275                 280                 285

Val Ile Ser Gln His Asn Ile Thr Gly Ile Gln Trp Val Gly Ser Glu
            290                 295                 300

Ser Trp Ile Thr Ser Arg Thr Leu Ala Glu Thr Lys Glu Tyr Ser Phe
305                 310                 315                 320

Leu Ser Gly Ala Val Gly Phe Ala Ile Ala Asn Ala Lys Leu Met Gly
                325                 330                 335

Leu Arg Glu Phe Leu Val Asn Val His Pro Asp Gln Glu Pro Asn Asn
            340                 345                 350

Glu Leu Leu Lys Glu Phe Trp Glu Thr Thr Phe Gln Cys Ser Leu Ser
            355                 360                 365

Asn Ser Gly Ser Gly Gly Cys Thr Gly Ser Glu Arg Ile Ala Glu Leu
            370                 375                 380

Gln Asn Glu Tyr Thr Asp Val Ser Glu Leu Arg Ile Ala Asn Lys Val
385                 390                 395                 400

Tyr Thr Ala Val Tyr Ala Ile Ala Gln Thr Leu His Asn Ile Leu Lys
                405                 410                 415

Asp Ile Lys Ser Ser Thr Lys Ser Lys Gly Glu Arg Pro Thr Pro
            420                 425                 430

Gln Lys Val Leu Glu Tyr Ile Gly Gly Val Lys Phe Thr Val Lys Thr
            435                 440                 445

Gly Glu Glu Ile Phe Phe Asp Ala Ser Gly Asn Pro Val Ala Arg Tyr
            450                 455                 460

Asp Leu Val Asn Trp Gln Pro Val Gln Asp Gly Ser Leu Gln Phe Lys
465                 470                 475                 480

Asn Val Gly Phe Tyr Asp Ser Ser Leu Pro Ser Glu Gln His Leu Gln
                485                 490                 495

Val Asn Gln Glu His Ile Leu Trp Thr Gly Asp Ser Gly Gln Leu Pro
```

```
                    500                 505                 510
        Val Ser Val Cys Ser Glu Thr Cys Pro Pro Gly Thr Arg Lys Ala Val
                515                 520                 525

Gln Lys Gly Arg Pro Val Cys Cys Tyr Asp Cys Ile Pro Cys Gly Glu
            530                 535                 540

Gly Glu Ile Ser Asn Gly Thr Asp Ser Asn Asp Cys Phe Pro Cys Asp
        545                 550                 555                 560

Leu Glu Tyr Trp Ser Asn Glu Ser Asn Asp Arg Cys Val Leu Lys Val
                        565                 570                 575

Ile Glu Phe Leu Ser Tyr Thr Glu Ile Met Gly Met Val Leu Cys Ile
                    580                 585                 590

Phe Ser Phe Ile Gly Val Leu Leu Thr Thr Ile Val Ser Phe Leu Phe
                595                 600                 605

Tyr Leu His Lys Glu Thr Pro Ile Val Arg Ala Asn Asn Ser Glu Leu
            610                 615                 620

Ser Phe Leu Leu Leu Phe Ser Leu Thr Leu Cys Phe Leu Cys Ser Leu
        625                 630                 635                 640

Thr Phe Ile Gly Arg Pro Thr Glu Trp Ser Cys Met Leu Arg His Thr
                        645                 650                 655

Ala Phe Gly Ile Thr Phe Val Leu Cys Ile Ser Cys Ile Leu Gly Lys
                    660                 665                 670

Thr Ile Val Val Leu Met Ala Phe Lys Ala Thr Leu Pro Gly Ser Asn
                675                 680                 685

Val Met Lys Trp Phe Gly Pro Leu Gln Gln Gln Leu Ser Val Val Ser
            690                 695                 700

Leu Thr Leu Ile Gln Met Ile Ile Cys Val Leu Trp Leu Thr Ile Ser
        705                 710                 715                 720

Pro Pro Phe Pro Tyr Met Asn Leu Ser Tyr Tyr Arg Glu Lys Ile Ile
                        725                 730                 735

Leu Glu Cys Asn Val Gly Ser Asp Leu Ala Phe Trp Ala Val Leu Gly
                    740                 745                 750

Tyr Thr Gly Leu Leu Ser Ile Leu Cys Phe Val Leu Ala Phe Leu Ala
                755                 760                 765

Arg Lys Leu Pro Asp Asn Phe Asn Glu Ala Lys Phe Ile Thr Phe Ser
            770                 775                 780

Met Leu Ile Phe Cys Ala Val Trp Leu Thr Phe Ile Pro Ala Tyr Val
        785                 790                 795                 800

Ser Ser Pro Gly Lys Phe Thr Val Ala Val Glu Ile Phe Ala Ile Leu
                        805                 810                 815

Ala Ser Ser Phe Ser Leu Leu Phe Cys Ile Phe Ala Pro Lys Cys Tyr
                    820                 825                 830

Ile Ile Leu Leu Lys Pro Glu Lys Xaa His Lys Glu Thr Asn Asp Gly
                835                 840                 845

Xaa Lys His Met Gln Ser Leu Trp
            850                 855

<210> SEQ ID NO 9
<211> LENGTH: 2923
<212> TYPE: DNA
<213> ORGANISM: Carassius auratus
<220> FEATURE:
<221> NAME/KEY: CDS
<222> LOCATION: (39)..(2600)

<400> SEQUENCE: 9
```

-continued

```
cccgggtcga cccacgcgtc cgcatacata ctactggt atg gca aag agc act gtg        56
                                         Met Ala Lys Ser Thr Val
                                           1               5 tca ctg ctt cta ctg ctg gtg gtg gtg cat ggt gtc ttt gtg cca gct          104
Ser Leu Leu Leu Leu Leu Val Val Val His Gly Val Phe Val Pro Ala
             10                  15                  20 tca gca caa ctc tgc agt ctg ctt ggt cac tct gca ttt cct gta ctt          152
Ser Ala Gln Leu Cys Ser Leu Leu Gly His Ser Ala Phe Pro Val Leu
         25                  30                  35 tct gca gaa aga gac atc aac att gga gca att ttc tca att cac aga          200
Ser Ala Glu Arg Asp Ile Asn Ile Gly Ala Ile Phe Ser Ile His Arg
 40                  45                  50 agt gct ctg cta aag atg cac cct ttc act tcc aaa cca gag cca aca          248
Ser Ala Leu Leu Lys Met His Pro Phe Thr Ser Lys Pro Glu Pro Thr
 55                  60                  65                  70 aca tgc ctc agg tta aac ttg cgt gaa ttt aaa ttt gct cag aca ttt          296
Thr Cys Leu Arg Leu Asn Leu Arg Glu Phe Lys Phe Ala Gln Thr Phe
             75                  80                  85 att ttt gcc att gag gag ata aat aac agc aca cag ctt ttg cct gga          344
Ile Phe Ala Ile Glu Glu Ile Asn Asn Ser Thr Gln Leu Leu Pro Gly
             90                  95                 100 gtt tct ttg ggt tat aaa ata tac gat gcc tgt aac tct ata gca ttg          392
Val Ser Leu Gly Tyr Lys Ile Tyr Asp Ala Cys Asn Ser Ile Ala Leu
            105                 110                 115 gct atc ctc tca ggc atg tct ttg atg aat ggt tat gaa aat att ttg          440
Ala Ile Leu Ser Gly Met Ser Leu Met Asn Gly Tyr Glu Asn Ile Leu
        120                 125                 130 agt gat ata tcc tgc tct cga tca cca gct gtc cag gcc att gtt gga          488
Ser Asp Ile Ser Cys Ser Arg Ser Pro Ala Val Gln Ala Ile Val Gly
135                 140                 145                 150 gag tcg aca tct tct cct acc ata gct ttg gct act gtg gtt ggg gca          536
Glu Ser Thr Ser Ser Pro Thr Ile Ala Leu Ala Thr Val Val Gly Ala
                155                 160                 165 ttc aac ata cct gtt atc agt cat ttt gcc aca tgc acg tgc ctg aat          584
Phe Asn Ile Pro Val Ile Ser His Phe Ala Thr Cys Thr Cys Leu Asn
            170                 175                 180 aac agg aaa ata tat cca tcc ttc ttt aga aca ata ccc agt gat tat          632
Asn Arg Lys Ile Tyr Pro Ser Phe Phe Arg Thr Ile Pro Ser Asp Tyr
            185                 190                 195 tac caa agc aga gcg ctg gca cag ctt gtc aag tat ttt ggc tgg acc          680
Tyr Gln Ser Arg Ala Leu Ala Gln Leu Val Lys Tyr Phe Gly Trp Thr
200                 205                 210 tgg gtt ggg acg gtc agg agt cgc agt gac tat ggt aat aat ggg ata          728
Trp Val Gly Thr Val Arg Ser Arg Ser Asp Tyr Gly Asn Asn Gly Ile
215                 220                 225                 230 gca gca ttt gaa gag gct gca aaa caa gaa ggt att tgc att gaa tat          776
Ala Ala Phe Glu Glu Ala Ala Lys Gln Glu Gly Ile Cys Ile Glu Tyr
                235                 240                 245 tca gaa gct gta tta aga act gat cca cca gag cag ttt ctg aag aca          824
Ser Glu Ala Val Leu Arg Thr Asp Pro Pro Glu Gln Phe Leu Lys Thr
            250                 255                 260 ctg gaa gtg att aaa aag ggc aca gcc agg gtt gtg gtg gct ttt atc          872
Leu Glu Val Ile Lys Lys Gly Thr Ala Arg Val Val Val Ala Phe Ile
            265                 270                 275 tca ttt gga gat ttt gcc ccc ctt gtg aaa gta att gca gaa caa aac          920
Ser Phe Gly Asp Phe Ala Pro Leu Val Lys Val Ile Ala Glu Gln Asn
        280                 285                 290 atc aca ggg ctg cag tgg gtt ggc agt gaa tcc tgg ata aca tct cga          968
Ile Thr Gly Leu Gln Trp Val Gly Ser Glu Ser Trp Ile Thr Ser Arg
295                 300                 305                 310
```

```
aat ctt gca gaa acc aag gaa tac agt ttc ctt tct gga gct gtg ggc      1016
Asn Leu Ala Glu Thr Lys Glu Tyr Ser Phe Leu Ser Gly Ala Val Gly
            315                 320                 325 ttt gct gta gta aat gcc aag ctt ctg ggt ctg cga gag ttc cta gtg      1064
Phe Ala Val Val Asn Ala Lys Leu Leu Gly Leu Arg Glu Phe Leu Val
        330                 335                 340 aat gtg aac cct aat caa gaa cta aaa aat gaa ctt tta aag gaa ttc      1112
Asn Val Asn Pro Asn Gln Glu Leu Lys Asn Glu Leu Leu Lys Glu Phe
    345                 350                 355 tgg gaa aca gct ttt cag tgt tct ttc aga tcc agt ggt agt aat gcc      1160
Trp Glu Thr Ala Phe Gln Cys Ser Phe Arg Ser Ser Gly Ser Asn Ala
360                 365                 370 tgt act ggc tca gag aaa ctg gca gag ctg caa aat gaa tat act gat      1208
Cys Thr Gly Ser Glu Lys Leu Ala Glu Leu Gln Asn Glu Tyr Thr Asp
375                 380                 385                 390 gta tct gag cta cga ata gaa cat aaa gct tac act gca gtg tat gct      1256
Val Ser Glu Leu Arg Ile Glu His Lys Ala Tyr Thr Ala Val Tyr Ala
            395                 400                 405 gtt gca cac aca ctg cat aat gtt tta aaa gac ttt aaa tca tcc acc      1304
Val Ala His Thr Leu His Asn Val Leu Lys Asp Phe Lys Ser Ser Thr
                410                 415                 420 aac aac agc aaa gga gag ctg ccc aca cca aaa aaa gta ttg caa tat      1352
Asn Asn Ser Lys Gly Glu Leu Pro Thr Pro Lys Lys Val Leu Gln Tyr
            425                 430                 435 atg aga gat gtg agc ttc act atg aaa aca ggt gag aat ata ttt ttt      1400
Met Arg Asp Val Ser Phe Thr Met Lys Thr Gly Glu Asn Ile Phe Phe
        440                 445                 450 gat gca agt ggt gat cca gtg gca ata tat gac ctg gtg aac tgg cag      1448
Asp Ala Ser Gly Asp Pro Val Ala Ile Tyr Asp Leu Val Asn Trp Gln
455                 460                 465                 470 cct gct gag gat gga aga tta cag ttc gag aat gtg ggt gtc tat gac      1496
Pro Ala Glu Asp Gly Arg Leu Gln Phe Glu Asn Val Gly Val Tyr Asp
            475                 480                 485 agc tca ctg cct tta gag caa cgt ctt caa gtt aat cag gaa cac ata      1544
Ser Ser Leu Pro Leu Glu Gln Arg Leu Gln Val Asn Gln Glu His Ile
                490                 495                 500 cta tgg gca ggg aag aga gca cag ttg cct ggg tcc gtg tgc agt gaa      1592
Leu Trp Ala Gly Lys Arg Ala Gln Leu Pro Gly Ser Val Cys Ser Glu
            505                 510                 515 agc tgc ccc act gga act aga aag act gtg cag aaa ggt cgg cct gtt      1640
Ser Cys Pro Thr Gly Thr Arg Lys Thr Val Gln Lys Gly Arg Pro Val
        520                 525                 530 tgc tgt tat gac tgt act cca tgt gca gaa gga gaa atc agt aat agc      1688
Cys Cys Tyr Asp Cys Thr Pro Cys Ala Glu Gly Glu Ile Ser Asn Ser
535                 540                 545                 550 aca gat tct agt gac tgc ttt cct tgt gat ttg gag tac tgg tcg aat      1736
Thr Asp Ser Ser Asp Cys Phe Pro Cys Asp Leu Glu Tyr Trp Ser Asn
            555                 560                 565 gaa agc aga gac aga tgt gta tta aaa gtg gtt gaa ttc ctt tcc tat      1784
Glu Ser Arg Asp Arg Cys Val Leu Lys Val Val Glu Phe Leu Ser Tyr
        570                 575                 580 aca gaa atc atg ggg atg gtg ctt tgc att ttc tcc ttc att ggc gta      1832
Thr Glu Ile Met Gly Met Val Leu Cys Ile Phe Ser Phe Ile Gly Val
    585                 590                 595 tta tta aca gca atg gta tct ttt ctg ttt tat ctc cat aaa gaa aca      1880
Leu Leu Thr Ala Met Val Ser Phe Leu Phe Tyr Leu His Lys Glu Thr
600                 605                 610 cct att gta aga gcc aac aac tca gag ctg agc ttc ctg ttg ctc ttc      1928
Pro Ile Val Arg Ala Asn Asn Ser Glu Leu Ser Phe Leu Leu Leu Phe
```

```
                615               620              625              630
tca ctc tca ctg tgt ttt ctc tgt tca cta act ttc att ggc cgg ccc              1976
Ser Leu Ser Leu Cys Phe Leu Cys Ser Leu Thr Phe Ile Gly Arg Pro
                635              640              645 act gag ctg tcc tgt atg ttg cgt cac aca gca ttt ggg atc act ttt              2024
Thr Glu Leu Ser Cys Met Leu Arg His Thr Ala Phe Gly Ile Thr Phe
        650              655              660 gtc ctt tgt atc tcc tgt gtt ctg ggg aaa aca ttg gta gtt tta atg              2072
Val Leu Cys Ile Ser Cys Val Leu Gly Lys Thr Leu Val Val Leu Met
            665              670              675 gcc ttc aga gct acg ctt cca gga agt gat gtc atg aaa tgg ttt ggg              2120
Ala Phe Arg Ala Thr Leu Pro Gly Ser Asp Val Met Lys Trp Phe Gly
        680              685              690 cct gca cag cag cga ctc agt gtt gtt tcc tta aca tta ata cag gtg              2168
Pro Ala Gln Gln Arg Leu Ser Val Val Ser Leu Thr Leu Ile Gln Val
695              700              705              710 att gtc tgt gtg ctt tgg tta aca ata tcc cct cct ttc cca tat atg              2216
Ile Val Cys Val Leu Trp Leu Thr Ile Ser Pro Pro Phe Pro Tyr Met
            715              720              725 aat tta agc tat tat aga gaa aaa ata att cta gaa tgt aat gta ggt              2264
Asn Leu Ser Tyr Tyr Arg Glu Lys Ile Ile Leu Glu Cys Asn Val Gly
        730              735              740 tca gct ctt ggt ttc tgg act gtt ctg tgt tat act ggc ctg cta tca              2312
Ser Ala Leu Gly Phe Trp Thr Val Leu Cys Tyr Thr Gly Leu Leu Ser
        745              750              755 agc ttg tgt ttt gtt tta gct ttt ctt gct cgg aag ctc cct gat aac              2360
Ser Leu Cys Phe Val Leu Ala Phe Leu Ala Arg Lys Leu Pro Asp Asn
760              765              770 ttc aat gag gcc aag ttc atc aca ttc agc atg ctc ata ttc tgt gct              2408
Phe Asn Glu Ala Lys Phe Ile Thr Phe Ser Met Leu Ile Phe Cys Ala
775              780              785              790 gtc tgg ctc aca ttt atc cca gct tat gtc agt tct cct gga aaa ttt              2456
Val Trp Leu Thr Phe Ile Pro Ala Tyr Val Ser Ser Pro Gly Lys Phe
            795              800              805 act gta gct gtg gag ata ttt gcc att tta gtt tca agt ttt ggt tta              2504
Thr Val Ala Val Glu Ile Phe Ala Ile Leu Val Ser Ser Phe Gly Leu
        810              815              820 cta ttt tgc ata ttt gcc cca aaa tgt tac ata att ttg cta aaa cca              2552
Leu Phe Cys Ile Phe Ala Pro Lys Cys Tyr Ile Ile Leu Leu Lys Pro
        825              830              835 gag aaa aac aca aag aaa caa atg atg ggg aaa tct tct aca gct ctt              2600
Glu Lys Asn Thr Lys Lys Gln Met Met Gly Lys Ser Ser Thr Ala Leu
840              845              850 tgaaacaaga gttaatcata taactgatta aaagccaaca tagccagctc tatcaaatgc             2660
atttctccca caggctgtgg caggctctgc agtgtaggcc gggtcagcac tagacacagt             2720
ggactctcag tgaccatctc catcacagcc atattctgga cctgcattat gtactttcta             2780
ataagaaatg atattgactt ttygcagtta acaacaaatg gaagttactt tttaatgtat             2840
tgaatttata tctttagttt tctagatttt ctacatmact gttgttttaa cmgtaaatag             2900
tatagacmtt gtggsggcsc ccc                                                     2923

<210> SEQ ID NO 10
<211> LENGTH: 854
<212> TYPE: PRT
<213> ORGANISM: Carassius auratus

<400> SEQUENCE: 10

Met Ala Lys Ser Thr Val Ser Leu Leu Leu Leu Leu Val Val Val His
```

-continued

```
  1               5              10              15
Gly Val Phe Val Pro Ala Ser Ala Gln Leu Cys Ser Leu Leu Gly His
                 20              25              30

Ser Ala Phe Pro Val Leu Ser Ala Glu Arg Asp Ile Asn Ile Gly Ala
             35              40              45

Ile Phe Ser Ile His Arg Ser Ala Leu Leu Lys Met His Pro Phe Thr
         50              55              60

Ser Lys Pro Glu Pro Thr Thr Cys Leu Arg Leu Asn Leu Arg Glu Phe
 65              70              75              80

Lys Phe Ala Gln Thr Phe Ile Phe Ala Ile Glu Glu Ile Asn Asn Ser
                 85              90              95

Thr Gln Leu Leu Pro Gly Val Ser Leu Gly Tyr Lys Ile Tyr Asp Ala
             100             105             110

Cys Asn Ser Ile Ala Leu Ala Ile Leu Ser Gly Met Ser Leu Met Asn
         115             120             125

Gly Tyr Glu Asn Ile Leu Ser Asp Ile Ser Cys Ser Arg Ser Pro Ala
     130             135             140

Val Gln Ala Ile Val Gly Glu Ser Thr Ser Ser Pro Thr Ile Ala Leu
145             150             155             160

Ala Thr Val Val Gly Ala Phe Asn Ile Pro Val Ile Ser His Phe Ala
                 165             170             175

Thr Cys Thr Cys Leu Asn Asn Arg Lys Ile Tyr Pro Ser Phe Phe Arg
             180             185             190

Thr Ile Pro Ser Asp Tyr Tyr Gln Ser Arg Ala Leu Ala Gln Leu Val
         195             200             205

Lys Tyr Phe Gly Trp Thr Trp Val Gly Thr Val Arg Ser Arg Ser Asp
     210             215             220

Tyr Gly Asn Asn Gly Ile Ala Ala Phe Glu Glu Ala Lys Gln Glu
225             230             235             240

Gly Ile Cys Ile Glu Tyr Ser Glu Ala Val Leu Arg Thr Asp Pro Pro
                 245             250             255

Glu Gln Phe Leu Lys Thr Leu Glu Val Ile Lys Lys Gly Thr Ala Arg
             260             265             270

Val Val Ala Phe Ile Ser Phe Gly Asp Phe Ala Pro Leu Val Lys
         275             280             285

Val Ile Ala Glu Gln Asn Ile Thr Gly Leu Gln Trp Val Gly Ser Glu
     290             295             300

Ser Trp Ile Thr Ser Arg Asn Leu Ala Glu Thr Lys Glu Tyr Ser Phe
305             310             315             320

Leu Ser Gly Ala Val Gly Phe Ala Val Val Asn Ala Lys Leu Leu Gly
                 325             330             335

Leu Arg Glu Phe Leu Val Asn Val Asn Pro Asn Gln Glu Leu Lys Asn
             340             345             350

Glu Leu Leu Lys Glu Phe Trp Glu Thr Ala Phe Gln Cys Ser Phe Arg
         355             360             365

Ser Ser Gly Ser Asn Ala Cys Thr Gly Ser Glu Lys Leu Ala Glu Leu
     370             375             380

Gln Asn Glu Tyr Thr Asp Val Ser Glu Leu Arg Ile Glu His Lys Ala
385             390             395             400

Tyr Thr Ala Val Tyr Ala Val Ala His Thr Leu His Asn Val Leu Lys
                 405             410             415

Asp Phe Lys Ser Ser Thr Asn Asn Ser Lys Gly Glu Leu Pro Thr Pro
             420             425             430
```

```
Lys Lys Val Leu Gln Tyr Met Arg Asp Val Ser Phe Thr Met Lys Thr
            435                 440                 445
Gly Glu Asn Ile Phe Phe Asp Ala Ser Gly Asp Pro Val Ala Ile Tyr
        450                 455                 460
Asp Leu Val Asn Trp Gln Pro Ala Glu Asp Gly Arg Leu Gln Phe Glu
465                 470                 475                 480
Asn Val Gly Val Tyr Asp Ser Ser Leu Pro Leu Glu Gln Arg Leu Gln
                485                 490                 495
Val Asn Gln Glu His Ile Leu Trp Ala Gly Lys Arg Ala Gln Leu Pro
            500                 505                 510
Gly Ser Val Cys Ser Glu Ser Cys Pro Thr Gly Thr Arg Lys Thr Val
        515                 520                 525
Gln Lys Gly Arg Pro Val Cys Cys Tyr Asp Cys Thr Pro Cys Ala Glu
530                 535                 540
Gly Glu Ile Ser Asn Ser Thr Asp Ser Ser Asp Cys Phe Pro Cys Asp
545                 550                 555                 560
Leu Glu Tyr Trp Ser Asn Glu Ser Arg Asp Arg Cys Val Leu Lys Val
                565                 570                 575
Val Glu Phe Leu Ser Tyr Thr Glu Ile Met Gly Met Val Leu Cys Ile
            580                 585                 590
Phe Ser Phe Ile Gly Val Leu Leu Thr Ala Met Val Ser Phe Leu Phe
        595                 600                 605
Tyr Leu His Lys Glu Thr Pro Ile Val Arg Ala Asn Asn Ser Glu Leu
        610                 615                 620
Ser Phe Leu Leu Leu Phe Ser Leu Ser Leu Cys Phe Leu Cys Ser Leu
625                 630                 635                 640
Thr Phe Ile Gly Arg Pro Thr Glu Leu Ser Cys Met Leu Arg His Thr
                645                 650                 655
Ala Phe Gly Ile Thr Phe Val Leu Cys Ile Ser Cys Val Leu Gly Lys
            660                 665                 670
Thr Leu Val Val Leu Met Ala Phe Arg Ala Thr Leu Pro Gly Ser Asp
        675                 680                 685
Val Met Lys Trp Phe Gly Pro Ala Gln Gln Arg Leu Ser Val Val Ser
690                 695                 700
Leu Thr Leu Ile Gln Val Ile Val Cys Val Leu Trp Leu Thr Ile Ser
705                 710                 715                 720
Pro Pro Phe Pro Tyr Met Asn Leu Ser Tyr Tyr Arg Glu Lys Ile Ile
                725                 730                 735
Leu Glu Cys Asn Val Gly Ser Ala Leu Gly Phe Trp Thr Val Leu Cys
            740                 745                 750
Tyr Thr Gly Leu Leu Ser Ser Leu Cys Phe Val Leu Ala Phe Leu Ala
        755                 760                 765
Arg Lys Leu Pro Asp Asn Phe Asn Glu Ala Lys Phe Ile Thr Phe Ser
        770                 775                 780
Met Leu Ile Phe Cys Ala Val Trp Leu Thr Phe Ile Pro Ala Tyr Val
785                 790                 795                 800
Ser Ser Pro Gly Lys Phe Thr Val Ala Val Glu Ile Phe Ala Ile Leu
                805                 810                 815
Val Ser Ser Phe Gly Leu Leu Phe Cys Ile Phe Ala Pro Lys Cys Tyr
            820                 825                 830
Ile Ile Leu Leu Lys Pro Glu Lys Asn Thr Lys Lys Gln Met Met Gly
        835                 840                 845
```

Lys Ser Ser Thr Ala Leu
    850

<210> SEQ ID NO 11
<211> LENGTH: 2749
<212> TYPE: DNA
<213> ORGANISM: Carassius auratus
<220> FEATURE:
<221> NAME/KEY: CDS
<222> LOCATION: (19)..(2571)

<400> SEQUENCE: 11

| | | |
|---|---|---|
| cgacccacgc gtccggac atg gca aag tgg act tta tca gtg ctg caa ctg<br>                                 Met Ala Lys Trp Thr Leu Ser Val Leu Gln Leu<br>                                  1               5                      10 | 51 |
| ctg ctg gtg gtg tat ggg gtc agt gtg cct gca tta gcg caa atc tgc<br>Leu Leu Val Val Tyr Gly Val Ser Val Pro Ala Leu Ala Gln Ile Cys<br>               15                  20                        25 | 99 |
| aga ctg ctt ggt cag cct gcc ctt cct cta ctt tct gca caa aaa gac<br>Arg Leu Leu Gly Gln Pro Ala Leu Pro Leu Leu Ser Ala Gln Lys Asp<br>        30                      35                      40 | 147 |
| att aat att ggg gca att ttc tca ttt cac aaa agt gct ctg ctg aag<br>Ile Asn Ile Gly Ala Ile Phe Ser Phe His Lys Ser Ala Leu Leu Lys<br>45                      50                      55 | 195 |
| atc cag cct ttc act tct aaa cca aat cca aca aca tgc ggc agc ttc<br>Ile Gln Pro Phe Thr Ser Lys Pro Asn Pro Thr Thr Cys Gly Ser Phe<br>60                      65                      70                      75 | 243 |
| aac agc tta cgt ggg ttt aag tat gct cag aca ctc ata ttt aca att<br>Asn Ser Leu Arg Gly Phe Lys Tyr Ala Gln Thr Leu Ile Phe Thr Ile<br>               80                  85                        90 | 291 |
| gag gag att aat aac agc aaa cag ctg ttg cct ggt gtt tct ttg ggc<br>Glu Glu Ile Asn Asn Ser Lys Gln Leu Leu Pro Gly Val Ser Leu Gly<br>        95                      100                    105 | 339 |
| tac aag ata tat gat tcc tgt agc tct ata tct caa act gtt ctg tca<br>Tyr Lys Ile Tyr Asp Ser Cys Ser Ser Ile Ser Gln Thr Val Leu Ser<br>           110                   115                   120 | 387 |
| ggc atg tct tta atg aat gga tat gaa gag act ttg aat gat aca tcc<br>Gly Met Ser Leu Met Asn Gly Tyr Glu Glu Thr Leu Asn Asp Thr Ser<br>        125                    130                    135 | 435 |
| tgc tct aga cca cca gct gtt cat gcc att gtt gga gaa tca aac tcc<br>Cys Ser Arg Pro Pro Ala Val His Ala Ile Val Gly Glu Ser Asn Ser<br>140                      145                    150                    155 | 483 |
| tct ccc acc atg gca ctg gct tct ata gtt ggt cct ttc agc tta ccc<br>Ser Pro Thr Met Ala Leu Ala Ser Ile Val Gly Pro Phe Ser Leu Pro<br>               160                  165                    170 | 531 |
| gtt att agt cat ttt gcc aca tgt gca tgc ctg agt aac aga aaa agg<br>Val Ile Ser His Phe Ala Thr Cys Ala Cys Leu Ser Asn Arg Lys Arg<br>           175                   180                   185 | 579 |
| ttt ccg tca ttc ttc aga aca ata ccc agt gat tat tat caa agc aga<br>Phe Pro Ser Phe Phe Arg Thr Ile Pro Ser Asp Tyr Tyr Gln Ser Arg<br>        190                    195                    200 | 627 |
| gct ctc gct cag ctt gtc aag cac ttt ggc tgg acc tgg gtt ggg aca<br>Ala Leu Ala Gln Leu Val Lys His Phe Gly Trp Thr Trp Val Gly Thr<br>205                      210                    215 | 675 |
| gtc agg agt cgt gga gac tat ggc aat aat ggt att tca gca ttt gag<br>Val Arg Ser Arg Gly Asp Tyr Gly Asn Asn Gly Ile Ser Ala Phe Glu<br>220                      225                    230                    235 | 723 |
| gag gct gca aga caa gaa ggg att tgt att gaa tac tca gag gcc ata<br>Glu Ala Ala Arg Gln Glu Gly Ile Cys Ile Glu Tyr Ser Glu Ala Ile<br>               240                  245                    250 | 771 |
| tta agc aca gat cca aag gag cag ttt tta aag aca cta gaa gtg ata | 819 |

```
                Leu Ser Thr Asp Pro Lys Glu Gln Phe Leu Lys Thr Leu Glu Val Ile
                            255                 260                 265 aag aag ggc act gcc aag gta gtg ctg gct ttc gtt gca gta gga gat            867
Lys Lys Gly Thr Ala Lys Val Val Leu Ala Phe Val Ala Val Gly Asp
            270                 275                 280 ttt gtt ccc ctc tta aat gta att gcg caa cac aac atc aca ggg att            915
Phe Val Pro Leu Leu Asn Val Ile Ala Gln His Asn Ile Thr Gly Ile
    285                 290                 295 cag tgg gtt ggc agt gaa tct tgg atc act tat cga aca ttt gca gaa            963
Gln Trp Val Gly Ser Glu Ser Trp Ile Thr Tyr Arg Thr Phe Ala Glu
300                 305                 310                 315 aca aaa gaa tac agt ttc ctc tct gga gct gtg ggt ttt gct ata gca           1011
Thr Lys Glu Tyr Ser Phe Leu Ser Gly Ala Val Gly Phe Ala Ile Ala
                320                 325                 330 aat gct aaa ctt gtg ggc ctg aga gag ttc cta gta aat gtg cat cct           1059
Asn Ala Lys Leu Val Gly Leu Arg Glu Phe Leu Val Asn Val His Pro
            335                 340                 345 gat caa gaa cca aac aat aaa ctt tta aaa gaa ttc tgg gaa aca gtt           1107
Asp Gln Glu Pro Asn Asn Lys Leu Leu Lys Glu Phe Trp Glu Thr Val
        350                 355                 360 ttt cag tgc tct ttc aga agc aac agt agt ggt ggc tgt act ggc tcc           1155
Phe Gln Cys Ser Phe Arg Ser Asn Ser Ser Gly Gly Cys Thr Gly Ser
    365                 370                 375 gaa aaa ctg gca gag ctg caa aat gaa tat act gat gta tca gag cta           1203
Glu Lys Leu Ala Glu Leu Gln Asn Glu Tyr Thr Asp Val Ser Glu Leu
380                 385                 390                 395 cgg att gta aat aaa gtg tac act gca gtg tat gct att gca cat aca           1251
Arg Ile Val Asn Lys Val Tyr Thr Ala Val Tyr Ala Ile Ala His Thr
                400                 405                 410 cta cac aat gta tta aaa gac ttg aga tcc tcc acc aac agc agc aaa           1299
Leu His Asn Val Leu Lys Asp Leu Arg Ser Ser Thr Asn Ser Ser Lys
            415                 420                 425 gga gaa tgg cct aca cta caa aag gtg ttg aat tat atg agg gat gtg           1347
Gly Glu Trp Pro Thr Leu Gln Lys Val Leu Asn Tyr Met Arg Asp Val
        430                 435                 440 aga ttc act gtt aaa aca ggt gaa gaa atc ttc ttt gat tta agt ggt           1395
Arg Phe Thr Val Lys Thr Gly Glu Glu Ile Phe Phe Asp Leu Ser Gly
    445                 450                 455 gat cca gca gcg aga tat gac ctt att aac tgg cag cct gct gaa aat           1443
Asp Pro Ala Ala Arg Tyr Asp Leu Ile Asn Trp Gln Pro Ala Glu Asn
460                 465                 470                 475 gga agt ttg cag ttt aag tat gtg ggc tca tat gac agc tca ctg cca           1491
Gly Ser Leu Gln Phe Lys Tyr Val Gly Ser Tyr Asp Ser Ser Leu Pro
                480                 485                 490 ttc gaa cag tgt ctt caa gtc acc cag gaa caa atg ata tgg gca ggg           1539
Phe Glu Gln Cys Leu Gln Val Thr Gln Glu Gln Met Ile Trp Ala Gly
            495                 500                 505 aac agt agg cag ttc cct gtg tcc gtg tgc agt gag agc tgc ccc cca           1587
Asn Ser Arg Gln Phe Pro Val Ser Val Cys Ser Glu Ser Cys Pro Pro
        510                 515                 520 ggt act aga aaa gct gtg caa aag ggg cga cct gtt tgc tgc tat gac           1635
Gly Thr Arg Lys Ala Val Gln Lys Gly Arg Pro Val Cys Cys Tyr Asp
    525                 530                 535 tgt att cca tgt tcg gaa gga gaa ata aat aat gaa aca gat tct agt           1683
Cys Ile Pro Cys Ser Glu Gly Glu Ile Asn Asn Glu Thr Asp Ser Ser
540                 545                 550                 555 gac tgc ttt cct tgt gat ttg gag tac tgg tcg aat gaa ggc aaa gac           1731
Asp Cys Phe Pro Cys Asp Leu Glu Tyr Trp Ser Asn Glu Gly Lys Asp
                560                 565                 570
```

```
                                                  -continued aaa tgt gta tta aaa gtg gta gag ttc cta tcc tat aca gaa atc atg    1779
Lys Cys Val Leu Lys Val Val Glu Phe Leu Ser Tyr Thr Glu Ile Met
        575                 580                 585 ggg acg gtg ctt tgt att ttc tcc ttc ttt ggg atg tta tta aca gca    1827
Gly Thr Val Leu Cys Ile Phe Ser Phe Phe Gly Met Leu Leu Thr Ala
590                 595                 600 att gta tct ttt gtg ttt tat ctt cat aaa gaa acc cct att gtc aga    1875
Ile Val Ser Phe Val Phe Tyr Leu His Lys Glu Thr Pro Ile Val Arg
    605                 610                 615 gcc aac aac tca gag ctg agc ttc ctg ctg ctc ttc tca ctc tca ctg    1923
Ala Asn Asn Ser Glu Leu Ser Phe Leu Leu Leu Phe Ser Leu Ser Leu
620                 625                 630                 635 tgt ttc ctc tgt tca ctt act ttc att ggt agg cct act gag tgg tcc    1971
Cys Phe Leu Cys Ser Leu Thr Phe Ile Gly Arg Pro Thr Glu Trp Ser
            640                 645                 650 tgt atg ttg cgc cac aca gca ttt ggg gtc act ttt gtc ctc tgt atc    2019
Cys Met Leu Arg His Thr Ala Phe Gly Val Thr Phe Val Leu Cys Ile
                655                 660                 665 tcc tgt gtt ttg gga aaa aca ata gtg gtc tta atg gct ttc agg gct    2067
Ser Cys Val Leu Gly Lys Thr Ile Val Val Leu Met Ala Phe Arg Ala
        670                 675                 680 aca ctt cca gga agt aat gtt atg aaa tgt ttt ggg cct ctt caa cag    2115
Thr Leu Pro Gly Ser Asn Val Met Lys Cys Phe Gly Pro Leu Gln Gln
685                 690                 695 cga ttc agt gtt gtt tca tta tca tta ata cag atg ata ata tgt gtg    2163
Arg Phe Ser Val Val Ser Leu Ser Leu Ile Gln Met Ile Ile Cys Val
700                 705                 710                 715 ctt tgg tta aca ata tcc cca cct ttt cct ttt atg aat ttg agc tat    2211
Leu Trp Leu Thr Ile Ser Pro Pro Phe Pro Phe Met Asn Leu Ser Tyr
            720                 725                 730 tac aga gaa aag atc atc cta gaa tgt aac tta ggt tca gct ctt ggc    2259
Tyr Arg Glu Lys Ile Ile Leu Glu Cys Asn Leu Gly Ser Ala Leu Gly
                735                 740                 745 ttc tgg ggt gtt ctg ggt tat act ggc ttg cta tca att ttg tgt ttt    2307
Phe Trp Gly Val Leu Gly Tyr Thr Gly Leu Leu Ser Ile Leu Cys Phe
        750                 755                 760 att tta gct ttt ctt gct agg aaa ctc cct gat aat ttc aac gag gcc    2355
Ile Leu Ala Phe Leu Ala Arg Lys Leu Pro Asp Asn Phe Asn Glu Ala
765                 770                 775 aag ttc ata aca ttc agt atg ctc ata ttc tgt gct gta tgg atc aca    2403
Lys Phe Ile Thr Phe Ser Met Leu Ile Phe Cys Ala Val Trp Ile Thr
780                 785                 790                 795 ttt att cca gct tat gtc agt tct cct gga aaa ttt act gta gcc gtg    2451
Phe Ile Pro Ala Tyr Val Ser Ser Pro Gly Lys Phe Thr Val Ala Val
            800                 805                 810 cag ata ttt gct att tta gca tca agt ttt agt tta ctc ttt tgc ata    2499
Gln Ile Phe Ala Ile Leu Ala Ser Ser Phe Ser Leu Leu Phe Cys Ile
                815                 820                 825 ttt gct cca aaa tgt tac att att ttg cta aaa cca gag aaa aat aca    2547
Phe Ala Pro Lys Cys Tyr Ile Ile Leu Leu Lys Pro Glu Lys Asn Thr
        830                 835                 840 aag aaa caa ata atg ggg aaa tct taatctaaag ctctttaagc tcagagataa   2601
Lys Lys Gln Ile Met Gly Lys Ser
845                 850 ttgtgtaaat cacaaaaatg taagaaaac ttaatatatt cctctgtatt ctgagaatta   2661
aactagcaga taagtgaata caagtatttt gcctataaaa aaagtaaaaa gaaacctaa   2721 agaaaaaaaa aaaaaaaaaa agggcggc                                     2749
```

<210> SEQ ID NO 12
<211> LENGTH: 851
<212> TYPE: PRT
<213> ORGANISM: Carassius auratus

<400> SEQUENCE: 12

| | | | | | | | | | | | | | | |
|---|---|---|---|---|---|---|---|---|---|---|---|---|---|---|
| Met | Ala | Lys | Trp | Thr | Leu | Ser | Val | Leu | Gln | Leu | Leu | Val | Val | Tyr |
| 1 | | | | 5 | | | | | 10 | | | | | 15 |
| Gly | Val | Ser | Val | Pro | Ala | Leu | Ala | Gln | Ile | Cys | Arg | Leu | Leu | Gly | Gln |
| | | | 20 | | | | | 25 | | | | | 30 | | |
| Pro | Ala | Leu | Pro | Leu | Leu | Ser | Ala | Gln | Lys | Asp | Ile | Asn | Ile | Gly | Ala |
| | | | 35 | | | | | 40 | | | | | 45 | | |
| Ile | Phe | Ser | Phe | His | Lys | Ser | Ala | Leu | Leu | Lys | Ile | Gln | Pro | Phe | Thr |
| | 50 | | | | | 55 | | | | | 60 | | | | |
| Ser | Lys | Pro | Asn | Pro | Thr | Thr | Cys | Gly | Ser | Phe | Asn | Ser | Leu | Arg | Gly |
| 65 | | | | | 70 | | | | | 75 | | | | | 80 |
| Phe | Lys | Tyr | Ala | Gln | Thr | Leu | Ile | Phe | Thr | Ile | Glu | Glu | Ile | Asn | Asn |
| | | | | 85 | | | | | 90 | | | | | 95 | |
| Ser | Lys | Gln | Leu | Leu | Pro | Gly | Val | Ser | Leu | Gly | Tyr | Lys | Ile | Tyr | Asp |
| | | | | 100 | | | | | 105 | | | | | 110 | |
| Ser | Cys | Ser | Ser | Ile | Ser | Gln | Thr | Val | Leu | Ser | Gly | Met | Ser | Leu | Met |
| | | | | 115 | | | | | 120 | | | | | 125 | |
| Asn | Gly | Tyr | Glu | Glu | Thr | Leu | Asn | Asp | Thr | Ser | Cys | Ser | Arg | Pro | Pro |
| | 130 | | | | | 135 | | | | | 140 | | | | |
| Ala | Val | His | Ala | Ile | Val | Gly | Glu | Ser | Asn | Ser | Ser | Pro | Thr | Met | Ala |
| 145 | | | | | 150 | | | | | 155 | | | | | 160 |
| Leu | Ala | Ser | Ile | Val | Gly | Pro | Phe | Ser | Leu | Pro | Val | Ile | Ser | His | Phe |
| | | | | 165 | | | | | 170 | | | | | 175 | |
| Ala | Thr | Cys | Ala | Cys | Leu | Ser | Asn | Arg | Lys | Phe | Pro | Ser | Phe | Phe |
| | | | | 180 | | | | | 185 | | | | | 190 | |
| Arg | Thr | Ile | Pro | Ser | Asp | Tyr | Tyr | Gln | Ser | Arg | Ala | Leu | Ala | Gln | Leu |
| | | | 195 | | | | | 200 | | | | | 205 | | |
| Val | Lys | His | Phe | Gly | Trp | Thr | Trp | Val | Gly | Thr | Val | Arg | Ser | Arg | Gly |
| | | | 210 | | | | | 215 | | | | | 220 | | |
| Asp | Tyr | Gly | Asn | Asn | Gly | Ile | Ser | Ala | Phe | Glu | Glu | Ala | Ala | Arg | Gln |
| 225 | | | | | 230 | | | | | 235 | | | | | 240 |
| Glu | Gly | Ile | Cys | Ile | Glu | Tyr | Ser | Glu | Ala | Ile | Leu | Ser | Thr | Asp | Pro |
| | | | | 245 | | | | | 250 | | | | | 255 | |
| Lys | Glu | Gln | Phe | Leu | Lys | Thr | Leu | Glu | Val | Ile | Lys | Lys | Gly | Thr | Ala |
| | | | | 260 | | | | | 265 | | | | | 270 | |
| Lys | Val | Val | Leu | Ala | Phe | Val | Ala | Val | Gly | Asp | Phe | Val | Pro | Leu | Leu |
| | | | | 275 | | | | | 280 | | | | | 285 | |
| Asn | Val | Ile | Ala | Gln | His | Asn | Ile | Thr | Gly | Ile | Gln | Trp | Val | Gly | Ser |
| | 290 | | | | | 295 | | | | | 300 | | | | |
| Glu | Ser | Trp | Ile | Thr | Tyr | Arg | Thr | Phe | Ala | Glu | Thr | Lys | Glu | Tyr | Ser |
| 305 | | | | | 310 | | | | | 315 | | | | | 320 |
| Phe | Leu | Ser | Gly | Ala | Val | Gly | Phe | Ala | Ile | Ala | Asn | Ala | Lys | Leu | Val |
| | | | | 325 | | | | | 330 | | | | | 335 | |
| Gly | Leu | Arg | Glu | Phe | Leu | Val | Asn | Val | His | Pro | Asp | Gln | Glu | Pro | Asn |
| | | | | 340 | | | | | 345 | | | | | 350 | |
| Asn | Lys | Leu | Leu | Lys | Glu | Phe | Trp | Glu | Thr | Val | Phe | Gln | Cys | Ser | Phe |
| | | | | 355 | | | | | 360 | | | | | 365 | |
| Arg | Ser | Asn | Ser | Ser | Gly | Gly | Cys | Thr | Gly | Ser | Glu | Lys | Leu | Ala | Glu |
| | 370 | | | | | 375 | | | | | 380 | | | | |

```
Leu Gln Asn Glu Tyr Thr Asp Val Ser Glu Leu Arg Ile Val Asn Lys
385                 390                 395                 400

Val Tyr Thr Ala Val Tyr Ala Ile Ala His Thr Leu His Asn Val Leu
            405                 410                 415

Lys Asp Leu Arg Ser Ser Thr Asn Ser Ser Lys Gly Glu Trp Pro Thr
            420                 425                 430

Leu Gln Lys Val Leu Asn Tyr Met Arg Asp Val Arg Phe Thr Val Lys
            435                 440                 445

Thr Gly Glu Glu Ile Phe Phe Asp Leu Ser Gly Asp Pro Ala Ala Arg
450                 455                 460

Tyr Asp Leu Ile Asn Trp Gln Pro Ala Glu Asn Gly Ser Leu Gln Phe
465                 470                 475                 480

Lys Tyr Val Gly Ser Tyr Asp Ser Ser Leu Pro Phe Glu Gln Cys Leu
            485                 490                 495

Gln Val Thr Gln Glu Gln Met Ile Trp Ala Gly Asn Ser Arg Gln Phe
            500                 505                 510

Pro Val Ser Val Cys Ser Glu Ser Cys Pro Pro Gly Thr Arg Lys Ala
            515                 520                 525

Val Gln Lys Gly Arg Pro Val Cys Cys Tyr Asp Cys Ile Pro Cys Ser
530                 535                 540

Glu Gly Glu Ile Asn Asn Glu Thr Asp Ser Ser Asp Cys Phe Pro Cys
545                 550                 555                 560

Asp Leu Glu Tyr Trp Ser Asn Glu Gly Lys Asp Lys Cys Val Leu Lys
            565                 570                 575

Val Val Glu Phe Leu Ser Tyr Thr Glu Ile Met Gly Thr Val Leu Cys
            580                 585                 590

Ile Phe Ser Phe Phe Gly Met Leu Leu Thr Ala Ile Val Ser Phe Val
            595                 600                 605

Phe Tyr Leu His Lys Glu Thr Pro Ile Val Arg Ala Asn Asn Ser Glu
            610                 615                 620

Leu Ser Phe Leu Leu Leu Phe Ser Leu Ser Leu Cys Phe Leu Cys Ser
625                 630                 635                 640

Leu Thr Phe Ile Gly Arg Pro Thr Glu Trp Ser Cys Met Leu Arg His
            645                 650                 655

Thr Ala Phe Gly Val Thr Phe Val Leu Cys Ile Ser Cys Val Leu Gly
            660                 665                 670

Lys Thr Ile Val Val Leu Met Ala Phe Arg Ala Thr Leu Pro Gly Ser
            675                 680                 685

Asn Val Met Lys Cys Phe Gly Pro Leu Gln Gln Arg Phe Ser Val Val
            690                 695                 700

Ser Leu Ser Leu Ile Gln Met Ile Ile Cys Val Leu Trp Leu Thr Ile
705                 710                 715                 720

Ser Pro Pro Phe Pro Phe Met Asn Leu Ser Tyr Tyr Arg Glu Lys Ile
            725                 730                 735

Ile Leu Glu Cys Asn Leu Gly Ser Ala Leu Gly Phe Trp Gly Val Leu
            740                 745                 750

Gly Tyr Thr Gly Leu Leu Ser Ile Leu Cys Phe Ile Leu Ala Phe Leu
            755                 760                 765

Ala Arg Lys Leu Pro Asp Asn Phe Asn Glu Ala Lys Phe Ile Thr Phe
            770                 775                 780

Ser Met Leu Ile Phe Cys Ala Val Trp Ile Thr Phe Ile Pro Ala Tyr
785                 790                 795                 800

Val Ser Ser Pro Gly Lys Phe Thr Val Ala Val Gln Ile Phe Ala Ile
```

```
                    805                 810                 815
Leu Ala Ser Ser Phe Ser Leu Leu Phe Cys Ile Phe Ala Pro Lys Cys
                820                 825                 830
Tyr Ile Ile Leu Leu Lys Pro Glu Lys Asn Thr Lys Lys Gln Ile Met
            835                 840                 845
Gly Lys Ser
    850

<210> SEQ ID NO 13
<211> LENGTH: 2595
<212> TYPE: DNA
<213> ORGANISM: Brachydanio rerio (zebrafish)
<220> FEATURE:
<221> NAME/KEY: CDS
<222> LOCATION: (4)..(2592)

<400> SEQUENCE: 13 aac atg gat ttg atg agc ttc att ctc tta tgg gct ggg ctg atg aaa        48
    Met Asp Leu Met Ser Phe Ile Leu Leu Trp Ala Gly Leu Met Lys
    1               5                   10                  15 gtc gca gaa gcc tca att gca cag ttc agc cag ttg gga gcc tca gcc       96
Val Ala Glu Ala Ser Ile Ala Gln Phe Ser Gln Leu Gly Ala Ser Ala
                20                  25                  30 cct gga aac atc atc att gga gga ctt ttc ccc atc cat gag gca gtg      144
Pro Gly Asn Ile Ile Ile Gly Gly Leu Phe Pro Ile His Glu Ala Val
            35                  40                  45 gtg cca gta aac tac acc ggc aac aac agc atc tct gcc cct gag cat      192
Val Pro Val Asn Tyr Thr Gly Asn Asn Ser Ile Ser Ala Pro Glu His
        50                  55                  60 ccg gac tgc atc aga ttc tac aca aag ggt cta aat caa gct cta gcg      240
Pro Asp Cys Ile Arg Phe Tyr Thr Lys Gly Leu Asn Gln Ala Leu Ala
65                  70                  75 atg att aat gct gta gaa atg gca aac aaa tcc ccc atg ttg agc agt      288
Met Ile Asn Ala Val Glu Met Ala Asn Lys Ser Pro Met Leu Ser Ser
            80                  85                  90                  95 ttg aac att act cta gga tac cga atc tac gac aca tgt tct gat gtc      336
Leu Asn Ile Thr Leu Gly Tyr Arg Ile Tyr Asp Thr Cys Ser Asp Val
                100                 105                 110 acg act gca ctg cgg gct gtc cat gat att atg agg ccg ttc tca gac      384
Thr Thr Ala Leu Arg Ala Val His Asp Ile Met Arg Pro Phe Ser Asp
            115                 120                 125 tgt gaa tca cca gaa gac tca tct caa ccc gtc cag cca ata atg gca      432
Cys Glu Ser Pro Glu Asp Ser Ser Gln Pro Val Gln Pro Ile Met Ala
        130                 135                 140 gta att ggg acc act tca tcc gag atc tca atc gca gtt gct cga gat      480
Val Ile Gly Thr Thr Ser Ser Glu Ile Ser Ile Ala Val Ala Arg Asp
    145                 150                 155 ctc aac ctt cag atg ata cct cag att agt tac gca tct aca gcc acg      528
Leu Asn Leu Gln Met Ile Pro Gln Ile Ser Tyr Ala Ser Thr Ala Thr
160                 165                 170                 175 att ttg agt gat aaa agt cgt ttc cct gct ttc atg agg act gtg ccc      576
Ile Leu Ser Asp Lys Ser Arg Phe Pro Ala Phe Met Arg Thr Val Pro
                180                 185                 190 agt gat gag tat caa acc tgt gcc atg gcc aaa ctt cta aag tcc aac      624
Ser Asp Glu Tyr Gln Thr Cys Ala Met Ala Lys Leu Leu Lys Ser Asn
            195                 200                 205 aaa tgg agc tgg gtt ggc att atc att aca gat gga gat tat gga cgt      672
Lys Trp Ser Trp Val Gly Ile Ile Ile Thr Asp Gly Asp Tyr Gly Arg
        210                 215                 220 tct gcc ttg gaa ggt ttc ata cag cac acc gaa acg gag gga att tgc      720
```

```
Ser Ala Leu Glu Gly Phe Ile Gln His Thr Glu Thr Glu Gly Ile Cys
    225                 230                 235 atc gcc ttt aaa gca atc ctt cca gac tca cta gca gat caa cag aaa      768
Ile Ala Phe Lys Ala Ile Leu Pro Asp Ser Leu Ala Asp Gln Gln Lys
240                 245                 250                 255 cta aac aca gac atc gaa aac acc ttg aac atc att gaa aac aat ccg      816
Leu Asn Thr Asp Ile Glu Asn Thr Leu Asn Ile Ile Glu Asn Asn Pro
                260                 265                 270 aaa gtt aga gtg gtg atc tcg ttt gct aaa tcc tct caa atg cag ttg      864
Lys Val Arg Val Val Ile Ser Phe Ala Lys Ser Ser Gln Met Gln Leu
            275                 280                 285 cta ttt aag ggg ctg cag agt aga aac att tca aat aac atg gtg tgg      912
Leu Phe Lys Gly Leu Gln Ser Arg Asn Ile Ser Asn Asn Met Val Trp
        290                 295                 300 gtt gcc agt gat aac tgg tcg acg gct aaa cat att ctg aat gat ggt      960
Val Ala Ser Asp Asn Trp Ser Thr Ala Lys His Ile Leu Asn Asp Gly
    305                 310                 315 agc atc act gat att ggg aaa gtg ctg ggc ttt acc ttc aag agt gga     1008
Ser Ile Thr Asp Ile Gly Lys Val Leu Gly Phe Thr Phe Lys Ser Gly
320                 325                 330                 335 aat ttt aca tct ttt cat cag tac cta aag aat cta cag ttt gaa agt     1056
Asn Phe Thr Ser Phe His Gln Tyr Leu Lys Asn Leu Gln Phe Glu Ser
                340                 345                 350 gaa gat gag atg aac aat tca ttc ctg aag gaa ttt tta aaa ctc aac     1104
Glu Asp Glu Met Asn Asn Ser Phe Leu Lys Glu Phe Leu Lys Leu Asn
            355                 360                 365 gca ggc aat gct tcc aat acc gtg ctg gag ctg atg aaa agc acc aat     1152
Ala Gly Asn Ala Ser Asn Thr Val Leu Glu Leu Met Lys Ser Thr Asn
        370                 375                 380 ttg gac aag att ttc agc att gag atg gcc gtc act gct gtt gct aat     1200
Leu Asp Lys Ile Phe Ser Ile Glu Met Ala Val Thr Ala Val Ala Asn
    385                 390                 395 gct gtg gct aaa cta tgt gca gaa aga caa tgt cag gac tct aca gct     1248
Ala Val Ala Lys Leu Cys Ala Glu Arg Gln Cys Gln Asp Ser Thr Ala
400                 405                 410                 415 ctc cag cct tgg gag ctc ctt agg cag ttg cgg agc atc act ttt gag     1296
Leu Gln Pro Trp Glu Leu Leu Arg Gln Leu Arg Ser Ile Thr Phe Glu
                420                 425                 430 aat gga gga gaa atg tac aaa ttt gat gcg aat ttg ggt tat gat ctc     1344
Asn Gly Gly Glu Met Tyr Lys Phe Asp Ala Asn Leu Gly Tyr Asp Leu
            435                 440                 445 ttc ctg tgg gaa gga gat caa tct gac gaa cat gct gat gac ata ata     1392
Phe Leu Trp Glu Gly Asp Gln Ser Asp Glu His Ala Asp Asp Ile Ile
        450                 455                 460 gca gaa tat gat cca acc aaa ggt gga ttc cac tac ata cac aat gat     1440
Ala Glu Tyr Asp Pro Thr Lys Gly Gly Phe His Tyr Ile His Asn Asp
465                 470                 475 ctg agt gaa att aag aaa gtg gta tct agg tgt tca aac agc tgt cag     1488
Leu Ser Glu Ile Lys Lys Val Val Ser Arg Cys Ser Asn Ser Cys Gln
                480                 485                 490                 495 cca ggc cag tac aag aaa aca gca gag ggt cag cac aca tgc tgt tat     1536
Pro Gly Gln Tyr Lys Lys Thr Ala Glu Gly Gln His Thr Cys Cys Tyr
            500                 505                 510 gag tgc ctc acc tgt gtg gaa aac cat tat tcc aac ata aca gat gct     1584
Glu Cys Leu Thr Cys Val Glu Asn His Tyr Ser Asn Ile Thr Asp Ala
        515                 520                 525 gat gaa tgt tcc cca tgt gac agt gag agc atg tgg tca ttg gcc aac     1632
Asp Glu Cys Ser Pro Cys Asp Ser Glu Ser Met Trp Ser Leu Ala Asn
    530                 535                 540
```

-continued

```
agc act gaa tgt cat ccc aag gtt ttt gaa tac ttt gat tgg aac agt      1680
Ser Thr Glu Cys His Pro Lys Val Phe Glu Tyr Phe Asp Trp Asn Ser
    545                 550                 555 ggc ttc gct att gtc ctg ctg ata ctg gct gcc ctc ggc gtc ctt ctc      1728
Gly Phe Ala Ile Val Leu Leu Ile Leu Ala Ala Leu Gly Val Leu Leu
560                 565                 570                 575 ctc ttc ttc atg tcc gca cta ttc ttc tgg caa aga cac tct ccg gtg      1776
Leu Phe Phe Met Ser Ala Leu Phe Phe Trp Gln Arg His Ser Pro Val
                580                 585                 590 gtc aag gct gca ggc ggg ccg ctt tgt cat ctg atc ctt gtc tcc ctg      1824
Val Lys Ala Ala Gly Gly Pro Leu Cys His Leu Ile Leu Val Ser Leu
            595                 600                 605 ctg ggc agt ttt atc agt gtc gtt ttc ttt gta ggc gaa ccg agc gat      1872
Leu Gly Ser Phe Ile Ser Val Val Phe Phe Val Gly Glu Pro Ser Asp
        610                 615                 620 ttg aca tgc agg gca agg cag gtt atc ttc ggc ttc agc ttc acg ctg      1920
Leu Thr Cys Arg Ala Arg Gln Val Ile Phe Gly Phe Ser Phe Thr Leu
    625                 630                 635 tgc gtc tca tgc atc ctg gtc aag tcc tta aaa atc ctg ctg gcg ttc      1968
Cys Val Ser Cys Ile Leu Val Lys Ser Leu Lys Ile Leu Leu Ala Phe
640                 645                 650                 655 gag atg aac ttt gag ctg aag gag ctt ctc tgt atg ctc tat aag cca      2016
Glu Met Asn Phe Glu Leu Lys Glu Leu Leu Cys Met Leu Tyr Lys Pro
                660                 665                 670 tat atg att gtc agc gtc ggc atg ggg gta cag atc atc att tgc act      2064
Tyr Met Ile Val Ser Val Gly Met Gly Val Gln Ile Ile Ile Cys Thr
            675                 680                 685 gtt tgg ctg acc ttg tac aag ccg ttt aaa gac aaa gag gtg cag acc      2112
Val Trp Leu Thr Leu Tyr Lys Pro Phe Lys Asp Lys Glu Val Gln Thr
        690                 695                 700 gaa tcc att cta ctt gaa tgt aac gag gga ttc tat gtg atg ttt tgg      2160
Glu Ser Ile Leu Leu Glu Cys Asn Glu Gly Phe Tyr Val Met Phe Trp
705                 710                 715 tta atg ctg gga tat ata gct ttg ttg gct ttg ttc tgc ttc acg ttt      2208
Leu Met Leu Gly Tyr Ile Ala Leu Leu Ala Leu Phe Cys Phe Thr Phe
720                 725                 730                 735 gca tat ata gcc aga aaa cta cct cag aag tac aat gaa gcc aag ttc      2256
Ala Tyr Ile Ala Arg Lys Leu Pro Gln Lys Tyr Asn Glu Ala Lys Phe
                740                 745                 750 atc act ttc agc atg gtc atc tgc ctc atg gcg tgg atc atc ttc atc      2304
Ile Thr Phe Ser Met Val Ile Cys Leu Met Ala Trp Ile Ile Phe Ile
            755                 760                 765 ccg att cat gtc acc acc agt ggc aaa tac gtg ccg gct gtg gaa atg      2352
Pro Ile His Val Thr Thr Ser Gly Lys Tyr Val Pro Ala Val Glu Met
        770                 775                 780 gtt gtc att ctt att tca aac tat gga atc ctg agc tgt cac ttt ttg      2400
Val Val Ile Leu Ile Ser Asn Tyr Gly Ile Leu Ser Cys His Phe Leu
785                 790                 795 ccc aaa tct tac att att ctt ttc aaa aag gag cac aat act aaa gac      2448
Pro Lys Ser Tyr Ile Ile Leu Phe Lys Lys Glu His Asn Thr Lys Asp
800                 805                 810                 815 gca ttc atg aag aat gtt tat gaa tat gca aga aag agc gca gag aat      2496
Ala Phe Met Lys Asn Val Tyr Glu Tyr Ala Arg Lys Ser Ala Glu Asn
                820                 825                 830 atc aag ggc ttg acc ggg act gag ccg caa ttt aaa caa gag aat tcg      2544
Ile Lys Gly Leu Thr Gly Thr Glu Pro Gln Phe Lys Gln Glu Asn Ser
            835                 840                 845 gtc tac aca ata tcc aat ctg tca ttc gtg cct gaa gag aaa cac gaa      2592
Val Tyr Thr Ile Ser Asn Leu Ser Phe Val Pro Glu Glu Lys His Glu
        850                 855                 860
``` taa                                                                                         2595

<210> SEQ ID NO 14
<211> LENGTH: 863
<212> TYPE: PRT
<213> ORGANISM: Brachydanio rerio (zebrafish)

<400> SEQUENCE: 14

Met Asp Leu Met Ser Phe Ile Leu Leu Trp Ala Gly Leu Met Lys Val
 1               5                  10                  15

Ala Glu Ala Ser Ile Ala Gln Phe Ser Gln Leu Gly Ala Ser Ala Pro
            20                  25                  30

Gly Asn Ile Ile Ile Gly Gly Leu Phe Pro Ile His Glu Ala Val Val
        35                  40                  45

Pro Val Asn Tyr Thr Gly Asn Asn Ser Ile Ser Ala Pro Glu His Pro
    50                  55                  60

Asp Cys Ile Arg Phe Tyr Thr Lys Gly Leu Asn Gln Ala Leu Ala Met
65                  70                  75                  80

Ile Asn Ala Val Glu Met Ala Asn Lys Ser Pro Met Leu Ser Ser Leu
                85                  90                  95

Asn Ile Thr Leu Gly Tyr Arg Ile Tyr Asp Thr Cys Ser Asp Val Thr
            100                 105                 110

Thr Ala Leu Arg Ala Val His Asp Ile Met Arg Pro Phe Ser Asp Cys
        115                 120                 125

Glu Ser Pro Glu Asp Ser Ser Gln Pro Val Gln Pro Ile Met Ala Val
    130                 135                 140

Ile Gly Thr Thr Ser Ser Glu Ile Ser Ile Ala Val Ala Arg Asp Leu
145                 150                 155                 160

Asn Leu Gln Met Ile Pro Gln Ile Ser Tyr Ala Ser Thr Ala Thr Ile
                165                 170                 175

Leu Ser Asp Lys Ser Arg Phe Pro Ala Phe Met Arg Thr Val Pro Ser
            180                 185                 190

Asp Glu Tyr Gln Thr Cys Ala Met Ala Lys Leu Leu Lys Ser Asn Lys
        195                 200                 205

Trp Ser Trp Val Gly Ile Ile Ile Thr Asp Gly Asp Tyr Gly Arg Ser
    210                 215                 220

Ala Leu Glu Gly Phe Ile Gln His Thr Glu Thr Glu Gly Ile Cys Ile
225                 230                 235                 240

Ala Phe Lys Ala Ile Leu Pro Asp Ser Leu Ala Asp Gln Gln Lys Leu
                245                 250                 255

Asn Thr Asp Ile Glu Asn Thr Leu Asn Ile Ile Glu Asn Asn Pro Lys
            260                 265                 270

Val Arg Val Val Ile Ser Phe Ala Lys Ser Ser Gln Met Gln Leu Leu
        275                 280                 285

Phe Lys Gly Leu Gln Ser Arg Asn Ile Ser Asn Asn Met Val Trp Val
    290                 295                 300

Ala Ser Asp Asn Trp Ser Thr Ala Lys His Ile Leu Asn Asp Gly Ser
305                 310                 315                 320

Ile Thr Asp Ile Gly Lys Val Leu Gly Phe Thr Phe Lys Ser Gly Asn
                325                 330                 335

Phe Thr Ser Phe His Gln Tyr Leu Lys Asn Leu Gln Phe Glu Ser Glu
            340                 345                 350

Asp Glu Met Asn Asn Ser Phe Leu Lys Glu Phe Leu Lys Leu Asn Ala
        355                 360                 365

```
Gly Asn Ala Ser Asn Thr Val Leu Glu Leu Met Lys Ser Thr Asn Leu
    370                 375                 380

Asp Lys Ile Phe Ser Ile Glu Met Ala Val Thr Ala Val Ala Asn Ala
385                 390                 395                 400

Val Ala Lys Leu Cys Ala Glu Arg Gln Cys Gln Asp Ser Thr Ala Leu
                405                 410                 415

Gln Pro Trp Glu Leu Leu Arg Gln Leu Arg Ser Ile Thr Phe Glu Asn
            420                 425                 430

Gly Gly Glu Met Tyr Lys Phe Asp Ala Asn Leu Gly Tyr Asp Leu Phe
        435                 440                 445

Leu Trp Glu Gly Asp Gln Ser Asp Glu His Ala Asp Ile Ile Ala
    450                 455                 460

Glu Tyr Asp Pro Thr Lys Gly Phe His Tyr Ile His Asn Asp Leu
465                 470                 475                 480

Ser Glu Ile Lys Lys Val Val Ser Arg Cys Ser Asn Ser Cys Gln Pro
                485                 490                 495

Gly Gln Tyr Lys Lys Thr Ala Glu Gly Gln His Thr Cys Cys Tyr Glu
            500                 505                 510

Cys Leu Thr Cys Val Glu Asn His Tyr Ser Asn Ile Thr Asp Ala Asp
        515                 520                 525

Glu Cys Ser Pro Cys Asp Ser Glu Ser Met Trp Ser Leu Ala Asn Ser
530                 535                 540

Thr Glu Cys His Pro Lys Val Phe Glu Tyr Phe Asp Trp Asn Ser Gly
545                 550                 555                 560

Phe Ala Ile Val Leu Leu Ile Leu Ala Ala Leu Gly Val Leu Leu Leu
                565                 570                 575

Phe Phe Met Ser Ala Leu Phe Phe Trp Gln Arg His Ser Pro Val Val
            580                 585                 590

Lys Ala Ala Gly Gly Pro Leu Cys His Leu Ile Leu Val Ser Leu Leu
                595                 600                 605

Gly Ser Phe Ile Ser Val Val Phe Phe Val Gly Glu Pro Ser Asp Leu
        610                 615                 620

Thr Cys Arg Ala Arg Gln Val Ile Phe Gly Phe Ser Phe Thr Leu Cys
625                 630                 635                 640

Val Ser Cys Ile Leu Val Lys Ser Leu Lys Ile Leu Leu Ala Phe Glu
                645                 650                 655

Met Asn Phe Glu Leu Lys Glu Leu Leu Cys Met Leu Tyr Lys Pro Tyr
            660                 665                 670

Met Ile Val Ser Val Gly Met Gly Val Gln Ile Ile Cys Thr Val
            675                 680                 685

Trp Leu Thr Leu Tyr Lys Pro Phe Lys Asp Lys Glu Val Gln Thr Glu
    690                 695                 700

Ser Ile Leu Leu Glu Cys Asn Glu Gly Phe Tyr Val Met Phe Trp Leu
705                 710                 715                 720

Met Leu Gly Tyr Ile Ala Leu Leu Ala Leu Phe Cys Phe Thr Phe Ala
                725                 730                 735

Tyr Ile Ala Arg Lys Leu Pro Gln Lys Tyr Asn Glu Ala Lys Phe Ile
            740                 745                 750

Thr Phe Ser Met Val Ile Cys Leu Met Ala Trp Ile Ile Phe Ile Pro
        755                 760                 765

Ile His Val Thr Thr Ser Gly Lys Tyr Val Pro Ala Val Glu Met Val
770                 775                 780
```

-continued

```
Val Ile Leu Ile Ser Asn Tyr Gly Ile Leu Ser Cys His Phe Leu Pro
785                 790                 795                 800

Lys Ser Tyr Ile Ile Leu Phe Lys Lys Glu His Asn Thr Lys Asp Ala
            805                 810                 815

Phe Met Lys Asn Val Tyr Glu Tyr Ala Arg Lys Ser Ala Glu Asn Ile
            820                 825                 830

Lys Gly Leu Thr Gly Thr Glu Pro Gln Phe Lys Gln Glu Asn Ser Val
        835                 840                 845

Tyr Thr Ile Ser Asn Leu Ser Phe Val Pro Glu Glu Lys His Glu
    850                 855                 860
```

ODORANT RECEPTORS

CROSS-REFERENCE TO RELATED APPLICATION

This application claims priority under 35UCS120 to U.S. Ser. No. 60/144,766, also entitled Odorant Receptors, filed Jul. 20, 1999.

This research was supported by grants from the National Institute on Deafness and Other Communication Disorders (NIDCD) and the Office of Naval Research and from the National Science Foundation.

INTRODUCTION

1. Field of the Invention

The field of the invention is odorant receptors.

2. Background of the Invention

The detection and discrimination of the multitude of environmental stimuli by the vertebrate olfactory system results from the activation of olfactory neurons within the olfactory epithelium of the nose (reviewed by Shepherd, 1994; Buck, 1996). The first step in olfactory processing resides at the level of the interaction of odorous ligands with odorant receptors. A large multigene family thought to encode odorant receptors was initially identified in the rat (Buck and Axel, 1991). These receptors are predicted to exhibit a seven transmembrane domain topology characteristic of the superfamily of G protein-coupled receptors. The sizes of the receptor repertoires of different vertebrate species are extremely large and are estimated to contain between 100 and 1000 individual genes (Buck, 1996). These observations suggest that the initial step in olfactory discrimination is accomplished by the integration of signals from a large number of specific receptors, each capable of binding only a small number of structurally-related odorants. Consistent with this model, it has been shown that one rat odorant receptor can be activated by 7 to 10 carbon n-aliphatic aldehydes (Zhao et al., 1997; see also Krautwurst et al., 1998; Malnic et al., 1999). In invertebrates, the *C. elegans* odr-10 gene encodes a G protein-coupled receptor that is sharply tuned to respond to the odorant, diacetyl (Sengupta et al., 1996; Zhang et al., 1997).

Other olfactory G protein-coupled receptors unrelated to the receptor gene family first described by Buck and Axel (1991) have been identified in the vomeronasal organ (VNO) of mammals (Dulac and Axel, 1995; Herrada and Dulac, 1997; Matsunami and Buck, 1997; Ryba and Tirindelli, 1997). The VNO is a specialization of the peripheral olfactory system in higher vertebrates that receives non-volatile pheromonal and non-pheromonal cues (Halpern, 1987). The VNO receptors are encoded by two unrelated gene families; members of the VNR family are localized in a subpopulation of VNO neurons defined by their expression of the G protein alpha subunit, Gai2 (Dulac and Axel, 1995; Berghard and Buck, 1996; Jia and Halpern, 1996), whereas members of the V2R family are expressed predominantly in a separate subpopulation of Gao-expressing cells (Herrada and Dulac, 1997; Matsunami and Buck, 1997; Ryba and Tirindelli, 1997). Interestingly, the V2R receptors are structurally related to the calcium-sensing receptor (CaSR; Hebert and Brown, 1995) and metabotropic glutamate receptor (mGluR; Tanabe et al., 1992) families. While it has been proposed that both classes of VNO receptors comprise pheromone receptors, the actual function of these orphan receptors awaits a direct demonstration of their ligand binding or ligand activation properties.

As an approach toward identifying ligands for olfactory receptors, we have pursued an expression cloning strategy using the goldfish as a model system. Fish are thought to respond to a smaller range of odorants than terrestrial vertebrates and thus appear to possess a smaller repertoire of odorant receptors (Ngai et al., 1993b). Moreover, the odorants that fish detect are water soluble, and include amino acids (feeding cues), bile acids (nonreproductive social cues with possible roles in migration), and sex steroids and prostaglandins (sex pheromonal cues) (reviewed by Hara, 1994; Sorensen and Caprio, 1998). Electrophysiological studies have defined the sensitivities of fish olfactory systems to specific ligands, demonstrating, for example, thresholds for detection in the picomolar (for sex steroids) to nanomolar (for amino acids) range (Hara, 1994). Thus, the defined properties of odorant-evoked pathways in vivo provide an excellent starting point for the molecular and biochemical characterization of fish odorant receptors.

In the examples below, we describe the expression cloning of a cDNA encoding a goldfish odorant receptor preferentially tuned to recognize basic amino acids. This cDNA encodes a G protein-coupled receptor that shares significant similarity to receptor families that include the CaSR, mGluR, and V2R class of VNO receptors. Degenerate polymerase chain reaction (PCR) reveals other related sequences that are expressed in the goldfish olfactory epithelium. Together our results indicate that these receptors comprise a family of odorant receptors. Moreover, the characterization of the goldfish amino acid receptor's odorant tuning properties provides critical molecular parameters for considering models of molecular recognition and information coding in the olfactory system.

Aspects of this invention have been published by Speca et al. (Neuron 1999 July; 23(3):487–98).

SUMMARY OF THE INVENTION

The invention provides methods and compositions relating to odorant receptors, including a general expression cloning methodology which is useful for identifying novel G protein-coupled receptors and a novel family of odorant receptors and related nucleic acids, ligands, agonists and antagonists. These compositions provide a wide variety of applications such as screening for related receptors, and by modulating the function of the disclosed receptors by modulating their expression or contacting them with agonists, antagonist or ligands modulating reproductive/sexual and non-sexual social behaviors mediated via the olfactory system, reproductive physiologies and olfactory system regulated feeding behaviors, migratory behaviors and events such as conception, implantation, estrous and menstruation.

DESCRIPTION OF PARTICULAR EMBODIMENTS OF THE INVENTION

The following description of particular embodiments and examples are offered by way of illustration and not by way of limitation. While particularly directed and exemplified often in terms of goldfish R5.24, the following descriptions, including fragment limitations and assay utilizations, also apply to the other disclosed CaSR-like polypeptides and polynucleotides.

The subject domains provide R5.24 domain specific activity or function, such as R5.24-mediated olfaction, ligand signal transducing or transducing inhibitory activity and/or R5.24-specific binding target-binding or binding inhibitory activity. R5.24-specific activity or function may be determined by convenient in vitro, cell-based, or in vivo assays: e.g. in vitro binding assays, cell culture assays, in animals (e.g. gene therapy, transgenics, etc.), etc. The specific binding target may be a ligand, agonist or antagonist, a R5.24 regulating protein or other regulator that directly modulates R5.24 activity or its localization; or non-natural binding target such as a specific immune protein such as an antibody, or a R5.24 specific agent such as those identified in screening assays such as described below. R5.24-binding specificity may be assayed by binding equilibrium constants (usually at least about $10^7$ $M^{-1}$, preferably at least about $10^8$ $M^{-1}$, more preferably at least about $10^9$ $M^{-1}$), by the ability of the subject polypeptides to function as negative mutants in R5.24-expressing cells, to elicit R5.24 specific antibody in a heterologous host (e.g. a rodent or rabbit), etc.

Exemplary suitable R5.24 polypeptides (a) SEQ ID NO:02, or a functional deletion mutant thereof or a sequence about 60–70%, preferably about 70–80%, more preferably about 80–90%, more preferably about 90–95%, most preferably about 95–99% similar to the R5.24 sequence disclosed herein as determined by Best Fit analysis using default settings and/or (b) is encoded by a nucleic acid comprising a natural R5.24 encoding sequence (such as SEQ ID NO:01) or a fragment thereof at least 36, preferably at least 72, more preferably at least 144, most preferably at least 288 nucleotides in length which specifically hybridizes thereto. Suitable deletion mutants are readily screened in R5.24 binding or activation assays as described herein. Preferred R5.24 domains/deletion mutants/fragments comprise at least 8, preferably at least 16, more preferably at least 32, most preferably at least 64 consecutive residues of SEQ ID NO:2 and provide a R5.24 specific activity, such as R5.24-specific antigenicity and/or immunogenicity, especially when coupled to carrier proteins. The subject domains provide R5.24-specific antigens and/or immunogens, especially when coupled to carrier proteins. For example, peptides corresponding to R5.24-specific domains are covalently coupled to keyhole limpet antigen (KLH) and the conjugate is emulsified in Freunds complete adjuvant. Laboratory rabbits are immunized according to conventional protocol and bled. The presence of R5.24-specific antibodies is assayed by solid phase immunosorbant assays using immobilized R5.24 polypeptides. R5.24 specific antigenic and/or immunogenic peptides encompass diverged sequence regions, preferably diverged extracellular or cytosolic regions, as seen in alignments with related sequences human CaSR, Fugu Ca02.1, mouse V2R2 and rat mGluR1.

Suitable natural R5.24 encoding sequence fragments are of length sufficient to encode such R5.24 domains. In a particular embodiment, the R5.24 fragments comprise species specific fragments; such fragments are readily discerned from alignments. Exemplary such R5.24-1 immunogenic and/or antigenic peptides are shown in Table 1.

TABLE 1

Immunogenic R5.24-1 polypeptides eliciting R5.24-1 specific rabbit polyclonal antibody: R5.24 polypeptide-KLH conjugates immunized per protocol described above.

| RS.24 Polypeptide | Immunogenicity | R5.24 Polypeptide | Immunogenicity |
|---|---|---|---|
| SEQ ID NO:02, res. 1–10 | +++ | SEQ ID NO:02, res. 474–485 | +++ |
| SEQ ID NO:02, res. 29–41 | +++ | SEQ ID NO:02, res. 502–516 | +++ |
| SEQ ID NO:02, res. 75–87 | +++ | SEQ ID NO:02, res. 561–576 | +++ |
| SEQ ID NO:02, res. 92–109 | +++ | SEQ ID NO:02, res. 595–616 | +++ |
| SEQ ID NO:02, res. 132–141 | +++ | SEQ ID NO:02, res. 640–656 | +++ |
| SEQ ID NO:02, res. 192–205 | +++ | SEQ ID NO:02, res. 683–697 | +++ |
| SEQ ID NO:02, res. 258–269 | +++ | SEQ ID NO:02, res. 717–732 | +++ |
| SEQ ID NO:02, res. 295–311 | +++ | SEQ ID NO:02, res. 768–777 | +++ |
| SEQ ID NO:02, res. 316–330 | +++ | SEQ ID NO:02, res. 798–813 | +++ |
| SEQ ID NO:02, res. 373–382 | +++ | SEQ ID NO:02, res. 829–843 | +++ |
| SEQ ID NO:02, res. 403–422 | +++ | SEQ ID NO:02, res. 844–877 | +++ |
| SEQ ID NO:02, res. 436–442 | +++ | SEQ ID NO:02, res. 852–875 | +++ |

In one embodiment, the R5.24 polypeptides are encoded by a nucleic acid comprising SEQ ID NO:01 or a fragment thereof which hybridizes with a full-length strand thereof, preferably under stringent conditions. Such nucleic acids comprise at least 36, preferably at least 72, more preferably at least 144 and most preferably at least 288 nucleotides of SEQ ID NO:01. Demonstrating specific hybridization generally requires stringent conditions, for example, hybridizing in a buffer comprising 30% formamide in 5×SSPE (0.18 M NaCl, 0.01 M $NaPO_4$, pH7.7, 0.001 M EDTA) buffer at a temperature of 42° C. and remaining bound when subject to washing at 42° C. with 0.2×SSPE (Conditions I); preferably hybridizing in a buffer comprising 50% formamide in 5×SSPE buffer at a temperature of 42° C. and remaining bound when subject to washing at 42° C. with 0.2×SSPE buffer at 42° C. (Conditions II). Exemplary nucleic acids which hybridize with a strand of SEQ ID NO:01 are shown in Table 2.

TABLE 2

Exemplary nucleic acids which hybridize with a strand of SEQ ID NO:01 under Conditions I and/or II.

| R5.24 Nucleic Acid | Hybridization | R5.24 Nucleic Acid | Hybridization |
| --- | --- | --- | --- |
| SEQ ID NO:01, nucl. 1–47 | + | SEQ ID NO:01, nucl. 738–801 | + |
| SEQ ID NO:01, nucl. 58–99 | + | SEQ ID NO:01, nucl. 805–854 | + |
| SEQ ID NO:01, nucl. 95–138 | + | SEQ ID NO:01, nucl. 855–907 | + |
| SEQ ID NO:01, nucl. 181–220 | + | SEQ ID NO:01, nucl. 910–953 | + |
| SEQ ID NO:01, nucl. 261–299 | + | SEQ ID NO:01, nucl. 1007–1059 | + |
| SEQ ID NO:01, nucl. 274–315 | + | SEQ ID NO:01, nucl. 1147–1163 | + |
| SEQ ID NO:01, nucl. 351–389 | + | SEQ ID NO:01, nucl. 1258–1279 | + |
| SEQ ID NO:01, nucl. 450–593 | + | SEQ ID NO:01, nucl. 1375–1389 | + |
| SEQ ID NO:01, nucl. 524–546 | + | SEQ ID NO:01, nucl. 1581–1595 | + |
| SEQ ID NO:01, nucl. 561–608 | + | SEQ ID NO:01, nucl. 1621–1639 | + |
| SEQ ID NO:01, nucl. 689–727 | + | SEQ ID NO:01, nucl. 1744–1755 | + |
| SEQ ID NO:01, nucl. 708–737 | + | SEQ ID NO:01, nucl. 1951–1969 | + |

A wide variety of cell types express R5.24 polypeptides subject to regulation by the disclosed methods, including many neuronal cells, transformed cells, infected (e.g. virus) cells, etc. Ascertaining R5.24 binding or activation is readily effected by binding assays or cells function assays as disclosed herein. Accordingly, indications for the subject methods encompass a wide variety of cell types and function, etc. The target cell may reside in culture or in situ, i.e. within the natural host.

In another aspect, the invention provides methods of screening for agents which modulate R5.24-ligand interactions. These methods generally involve forming a mixture of a R5.24-expressing cell, a R5.24 ligand and a candidate agent, and determining the effect of the agent on the R5.24-ligand interaction. The methods are amenable to automated, cost-effective high throughput screening of chemical libraries for lead compounds. Identified reagents find use in the pharmaceutical industries for animal and human trials; for example, the reagents may be derivatized and rescreened in vitro and in vivo assays to optimize activity and minimize toxicity for pharmaceutical development.

The amino acid sequences of the disclosed R5.24 polypeptides are used to back-translate R5.24 polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural R5.24-encoding nucleic acid sequences ("GCG" software, Genetics Computer Group, Inc, Madison Wis.). R5.24-encoding nucleic acids are used in R5.24-expression vectors and incorporated into recombinant host cells, e.g. for expression and screening, etc.

The invention also provides nucleic acid hybridization probes and replication/amplification primers having a R5.24 cDNA specific sequence comprising a fragment of SEQ ID NO:1, and sufficient to effect specific hybridization thereto. Such primers or probes are at least 12, preferably at least 24, more preferably at least 36 and most preferably at least 96 nucleotides in length. Demonstrating specific hybridization generally requires stringent conditions, for example, hybridizing in a buffer comprising 30% formamide in 5×SSPE (0.18 M NaCl, 0.01 M $NaPO_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2 x SSPE buffer at 42° C. R5.24 nucleic acids can also be distinguished using alignment algorithms, such as BLASTX (Altschul et al. (1990) Basic Local Alignment Search Tool, J Mol Biol 215, 403–410). In addition, the invention provides nucleic acids having a sequence about 60–70%, preferably about 70–80%, more preferably about 80–90%, more preferably about 90–95%, most preferably about 95–99% similar to SEQ ID NO:1 as determined by Best Fit analysis using default settings.

The subject nucleic acids are of synthetic/non-natural sequences and/or are recombinant, meaning they comprise a non-natural sequence or a natural sequence joined to nucleotide(s) other than that which it is joined to on a natural chromosome. The subject recombinant nucleic acids comprising the nucleotide sequence of disclosed vertebrate R5.24 nucleic acids, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, more preferably fewer than 500 bp, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of R5.24 genes and gene transcripts and in detecting or amplifying nucleic acids encoding additional R5.24 homologs and structural analogs.

EXAMPLES

We have developed a general method for expression cloning novel G protein coupled receptors as a strategy for identifying vertebrate odorant receptors. The sensitivity and flexibility of this technique allows the activation of multiple G protein pathways to be detected, even when the relevant receptor mRNA constitutes as little as 0.1% of the injected RNA population. Thus, this system facilitates the functional identification of cDNAs corresponding to any G protein coupled receptor for which specific agonists are available. By using our expression cloning approach, we isolated from the goldfish olfactory epithelium a cDNA encoding a receptor that is activated by amino acid odorants. Characterization of this receptor, receptor 5.24, reveals that it is preferentially activated by arginine and lysine and interacts with these compounds with high affinity (Kd=~100 nM). Other amino acids bind to receptor 5.24 with lower affinity; parameters affecting binding specificity appear to include the structure and/or charge of the side chain's terminal functional moiety, as well as its backbone length. The receptor demonstrates stereospecificity and does not appear to bind amino acid neurotransmitters found in the peripheral olfactory system. The observed affinity of this cloned receptor agrees well with the in vivo threshold sensitivities of the goldfish olfactory system to arginine (ca. 1 nM). However, the cloned goldfish receptor appears to be different from basic amino acid binding sites characterized in isolated fish olfactory cilia, which show 50~100-fold lower affinities for ligand (e.g., Cagan and Zeiger, 1978).

It has been suggested that amino acid odorant stimuli are transduced by phospholipase-mediated pathways in fish (Huque and Bruch, 1986; Restrepo et al., 1993). Consistent with these observations, our results demonstrate that odorant activation of the cloned goldfish amino acid receptor leads to increased PI turnover in Xenopus oocytes as well as in mammalian cells. No coupling to G$\alpha$s-like pathways is observed even though these G protein subunits are present in both heterologous cell systems, indicating that the goldfish amino acid odorant receptor and all olfactory CaSR receptors, stimulate PI turnover in vivo. Interestingly, these receptors are expressed in microvillous neurons (see also Cao et al., 1998), which morphologically resemble the sensory neurons of the VNO. Both the VNO as well as fish olfactory microvillous neurons do not appear to express cyclic nucleotide-gated channel alpha subunits (Berghard et al., 1996), which are required for transducing odorant-evoked cAMP elevations into changes in membrane potential in mammalian ciliated olfactory neurons (Brunet et al., 1996).

Receptor 5.24 shares sequence similarity to previously identified G protein receptors, including the CaSR, mGluR, and V2R families (Nakanishi et al., 1990; Hebert and Brown, 1995; Herrada and Dulac, 1997; Matsunami and Buck, 1997; Ryba and Tirindelli, 1997). Additional CaSR-like receptors are also expressed in the goldfish olfactory epithelium. Our results indicate that receptor 5.24 is a member of a multigene family of receptors expressed by olfactory sensory neurons, and together with our biochemical characterization of this receptor provide direct evidence that the family of olfactory CaSR-like receptors are in fact odorant receptors.

The mammalian V2R receptors have been proposed to constitute a family of pheromone receptors based on their expression in the VNO (Herrada and Dulac, 1997; Matsunami and Buck, 1997; Ryba and Tirindelli, 1997). It should be noted, however, that the VNO—a specialization of the olfactory apparatus in terrestrial vertebrates—receives both pheromonal as well as non-pheromonal cues (Halpern, 1987). While the ligand specificities of the mammalian V2R receptors remain to be demonstrated, our data clearly show that at least one member of the goldfish receptor family, receptor 5.24, is an odorant receptor that recognizes a specific subset of amino acid stimuli. Since amino acid odorants are not pheromones, the family of olfactory CaSR-like receptors, including the mammalian V2R receptors, may in fact function to receive a wide variety of stimuli that includes both pheromonal and non-pheromonal odorants. We disclose that receptors related to receptor 5.24 are used by the fish to detect other amino acid odorants.

Electrophysiological recordings from isolated salmon olfactory neurons have demonstrated that ~60% of the cells are sensitive to 0.01–10 $\mu$M L-serine (Nevitt and Dittman, 1999). Similarly, single-unit recordings from the catfish olfactory epithelium have shown that ~40% of the olfactory neurons respond to 100 $\mu$M L-arginine (Kang and Caprio, 1995). Multi-unit recordings from the goldfish olfactory epithelium, where activity from ~5 cells was detected at each recording site, also suggest that a large fraction of olfactory neurons respond to arginine (25 out of 28 locations with spontaneous activity responded 100 $\mu$M L-arginine), but few appeared sensitive to pheromones (e.g., only 25 out of 65 locations responded to 0.1 $\mu$M 1 5-ketoprostaglandin F2a). Thus, the widespread expression of receptor 5.24 mRNA in goldfish olfactory neurons is consistent with electrophysiological recordings which independently suggest that a large fraction of fish olfactory neurons express amino acid odorant receptors.

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

General Strategy for Expression Cloning of Odorant Receptors. We elected to utilize the goldfish olfactory system, owing to the extensive physiological and behavioral characterization of its responses to both pheromonal and non-pheromonal olfactory stimuli in this species (Sorensen and Caprio, 1998; Sorensen et al., 1998). Our approach was designed to allow for the detection of receptor activation of multiple G protein-mediated pathways—whereas previous studies have demonstrated that odorant-evoked excitatory signaling in mammalian olfactory neurons is mediated exclusively by the intracellular second messenger, cAMP (Brunet et al., 1996), in vitro biochemical studies have suggested that stimulation of phosphatidyl inositol (PI) turnover, resulting in the production of the second messengers diacylglycerol and inositol 1,4,5-trisphosphate (IP3), may mediate olfactory signaling in fish (Huque and Bruch, 1986; Restrepo et al., 1993). Thus, for expression cloning of fish odorant receptors it seemed prudent to utilize a system capable of detecting activation of multiple signaling pathways.

The Xenopus oocyte provides a powerful method for expression cloning certain G protein-coupled receptors, owing to the ability to detect increases in PI turnover through the IP3-mediated release of Ca2+ from internal stores and the subsequent activation of Ca2+-dependent Cl-channels (Masu et al., 1987). This cell does not normally exhibit an electrophysiologic response to the activation of Gas (and therefore adenylyl cyclase), however. We therefore engineered the oocyte to provide a robust read-out for this G protein-dependent pathway (Lim et al., 1995). This method relies upon the ectopic expression of Gaolf (a Gas-like isoform highly enriched in olfactory cilia; Jones and Reed, 1989) and G protein-gated inwardly rectifying potassium channels (GIRKs), together with candidate receptors (Lim et al., 1995). Potassium currents can be observed in response to gating of GIRK channels by free G protein bg subunits following their dissociation from activated Gas-like or Gai subunits (Reuveny et al., 1994; Lim et al., 1995). To determine whether this system would be amenable to expression cloning, where a cDNA encoding the receptor of interest comprises only a small fraction of a pool of cDNAs, we injected into oocytes RNA encoding the dopamine D1 receptor together with Gaolf and GIRK RNAs, with the amount of receptor RNA diluted 1,000-fold prior to injection. We could typically elicit robust agonist-dependent currents in receptor-expressing oocytes. These controls indicated that a pool of ~1,000 cDNA clones containing a single receptor cDNA could still give rise to a detectable signal when expressed and activated in our assay system. Thus, oocytes expressing Gaolf and GIRK provide a means of expression cloning G protein-coupled receptors whose downstream coupling pathways are ambiguous.

Identification by Expression Cloning of a cDNA Encoding a Goldfish Odorant Receptor. RNA was synthesized from pools of goldfish olfactory cDNA clones (900 individual clones per pool) and injected into Xenopus oocytes together with synthetic RNAs encoding GIRK and Gaolf. Oocytes were then screened for responses upon exposure to odorant cocktails containing amino acids, bile acids, or sex pheromones. Odorants were tested at concentrations 100- to 1,000-fold higher than those required to elicit half-maximal physiological responses in vivo (Caprio, 1978; Sorensen et al., 1987; Sorensen et al., 1988; Michel and Lubomudrov, 1995; see Experimental Procedures); these concentrations did not elicit activity in oocytes injected only with GIRK and G protein RNAs. Oocytes injected with RNA from one pool, pool 19, demonstrated a robust response to amino acids, but not to bile acids or sex pheromones. The response to amino acids was biphasic, beginning with an oscillating inward current above the basal inward K+ current, followed by a decline in inward current to below the basal level. Such a biphasic effect is thought to be caused by Gaq-mediated activation of phospholipase C (responsible for the intial inward current via IP3) and protein kinase C (leading to suppression of the K+ current through phosphorylation of GIRK channel subunits) (Sharon et al., 1997). Indeed, the oscillating inward currents in response to amino acids were still observed in oocytes expressing pool 19 RNA without Gaolf or GIRK RNAs, suggesting that the receptor contained in this pool interacts with a phospholipase-mediated pathway.

Iterative subdivision of pool 19 by sib-selection allowed the isolation of a single clone encoding a receptor, designated receptor 5.24. Receptor 5.24 responds best to basic L-amino acids, showing roughly equivalent evoked currents upon activation by arginine and lysine, smaller responses to neutral aliphatic L-amino acids (e.g., methionine, isoleucine, threonine, serine, alanine) and little or no response to acidic and aromatic L-amino acids (e.g., glutamate, aspartate, tyrosine, phenylalanine, tryptophan, histidine); the receptor is not activated by D-amino acids (all amino acids referred to hereafter are L-isomers unless stated otherwise).

High-Affinity Binding of Radiolabeled L-Arginine to the Cloned Goldfish Odorant Receptor. To determine the affinity of the cloned goldfish amino acid receptor for basic amino acids, we characterized the ligand-receptor interaction by radiolabeled ligand binding to receptors expressed in mammalian cells. Human embryonic kidney (HEK) 293 cells were transfected with expression plasmids containing the receptor 5.24 cDNA insert. Membranes prepared from receptor 5.24-expressing cells exhibit saturable binding at concentrations of up to 1 mM 3H-arginine, and the extent of ligand binding is significantly higher than with membranes from control cells. Further analysis of specific binding activity from multiple experiments indicates a receptor with a single binding site (Hill coefficient=$0.95 \pm 0.07$ [mean±SEM], n=4 determinations) with a dissociation constant (Kd) of $121 \pm 33$ nM arginine (mean±SEM, n=4; range: 52–207 nM). We next wished to determine what second messenger pathway receptor 5.24 couples to in HEK 293 cells. Control cells or cells expressing receptor 5.24 were exposed to varying concentrations of arginine and assayed for the accumulation of IP3 and cAMP. Arginine elicits a specific increase in IP3 in receptor 5.24-expressing cells in a dose-dependent manner. By way of contrast, arginine at 0.1 mM or 10 mM does not cause a detectable change in cAMP levels in these cells, even though activation of b-adrenergic receptors (expressed endogenously by the host cell line) leads to increased cAMP accumulation. These results indicate that, as in Xenopus oocytes, receptor 5.24 preferentially stimulates PI turnover in HEK 293 cells.

Structure-Activity Properties of Compounds Interacting with the Cloned Goldfish Amino Acid Odorant Receptor. An understanding of how odorant receptors are used to encode olfactory information requires a characterization of the odorant specificities of individual receptor types. We therefore wished to determine the relative specificity of receptor 5.24 for structurally related ligands. Since this receptor binds to arginine with high affinity, we screened other compounds for receptor 5.24 binding by using a 3H-arginine displacement assay. While these assays do not give information regarding whether a compound functions as an agonist, partial agonist, or antagonist, they do nonetheless allow insight into the molecular specificity of the receptor. Briefly, 3H-arginine binding to membranes from receptor 5.24-expressing HEK 293 cells was assayed in the absence or presence of varying concentrations of competitor ligands. Consistent with their profiles of receptor 5.24 activation in Xenopus oocytes, arginine and lysine displace 3H-arginine binding with similar concentration dependencies, showing half-maximal inhibition (IC50) at ~0.3 and ~0.5 mM, respectively (corresponding to inhibition constants or Ki's of 80 and 90 nM; see Table 3). Glutamate, which does not appear to activate receptor 5.24 expressed in Xenopus oocytes, displaces 3H-arginine approximately 80-fold less well than either unlabeled arginine or lysine (IC50=~20 mM; Ki=6.7 mM). Interestingly, agmatine, a decarboxylated analogue of arginine, displaces 3H-arginine very poorly (Ki>1 mM; see below and Table 4).

TABLE 3

Binding Affinity of the Receptor for Amino Acids, Amino Acid Derivatives and Neurotransmitters. Binding affinity (Ki) was determined by the ability of the individual amino acids to displace 3H-L-arginine binding from membranes prepared from HEK 293 cells expressing receptor 5.24.

| AMINO ACID CLASS | AMINO ACID | Ki (µM) |
|---|---|---|
| Basic side chain | L-Arginine | 0.08 |
| | L-Lysine | 0.09 |
| Sulfur-containing side chain | L-Cysteine | 0.53 |
| | L-Methionine | 0.81 |
| Amide side chain | L-Glutamine | 0.32 |
| | L-Asparagine | 2.1 |
| Acidic side chain | L-Glutamate | 6.7 |
| | L-Aspartate | 27 |
| Long aliphatic side chain | L-Isoleucine | 2.2 |
| | L-Leucine | 4.4 |
| | L-Valine | 6.2 |
| Short aliphatic side chain | L-Serine | 2.8 |
| | L-Threonine | 3.2 |
| | L-Glycine | 3.9 |
| | L-Alanine | 5.6 |
| | L-Proline | 58 |
| Aromatic side chain | L-Tryptophan | 4.1 |
| | L-Phenylalanine | 5.8 |
| | L-Histidine | 13 |
| | L-Tyrosine | 16 |
| Arginine/Lysine derivatives | Agmatine | >1000 |
| | L-Citruline | 0.96 |
| | L-Ornithine | 1.00 |
| | L-Homoarginine | 1.63 |
| | L-NAME | 1.02 |
| | Cadaverine | >1000 |
| | Putrescine | >1000 |
| Neurotransmitters | γ-Aminobutyric Acid (GABA) | >1000 |
| | Taurine | >1000 |
| | Carnosine | >1000 |

TABLE 4

Odorant Cocktails Used for Screening the Goldfish Olfactory cDNA Library in Xenopus Oocyyes Amino Acids/Bile Acids

| | |
|---|---|
| L-Amino Acids (Final concentration 50 mM) | Serine, Alanine, Methionine, Glutamic Acid, Arginine, Glutamine, Lysine, Histidine |
| Bile Acids (Final concentration 1 mM) | Taurocholic Acid, Taurolithocholic Acid Sulfate, Taurodeoxycholic Acid, Taurochenodeoxycholic Acid, Glycocholic Acid, Prostaglandins/Sex Steroids |
| Prostaglandins (Final concentration 100 mM) | Prostaglandin F2a, 15-Ketoprostaglandin F2a |
| Sex Steroids (Final concentration 10 mM) | 17,20 b-dihydroxy-4-pregnen-3-one, 17,20 b-dihydroxy-4-pregnen-3-one Sulfate |

We performed comparative binding studies for 20 naturally occurring amino acids as well as amino acid analogues and neurotransmitters (Tables 3 and 4). A number of trends are evident from this analysis. First, receptor 5.24 apparently is tuned to recognize amino acids containing basic R group side chains; of the 20 amino acids tested, arginine and lysine display the highest affinities. In addition, ~10- to >100-fold lower affinities are observed with arginine and lysine analogues, and no specific interactions could be detected for the amino acid neurotransmitters g-amino butyric acid (GABA), carnosine, or taurine (Ki>1 mM), which are present in the peripheral olfactory system (Nicoll, 1971; Collins, 1974; Margolis, 1974). Second, the side chain's terminal functional group is an important parameter in determining specificity. Substitution of the basic side chain with R groups containing amide (glutamine, asparagine), sulfur-containing (cysteine, methionine), or carbamyl (citrulline) moieties results in a ~4- to ~25-fold decrease in affinity. Amino acids with side chains containing terminal amide or sulfur-containing groups in general demonstrate higher affinity than those with aliphatic side chains lacking these structures. Substitution with acidic side chains (glutamate, aspartate) results in a large (~80- to ~300-fold) decrease in affinity. Amino acids containing cyclized (proline) or aromatic (tryptophan, phenylalanine, histidine, tyrosine) side groups in general interact with receptor 5.24 with low affinities. Third, specificity is based in part on the R group's carbon backbone length, as illustrated by comparing lysine (Ki=0.09 mM) vs. ornithine (Ki=1.0 mM ; backbone shorter than lysine's by one carbon) and arginine (Ki=0.08 mM) vs. homoarginine (Ki=1.6 mM; backbone longer than arginine's by one carbon). Tuning of this receptor based on carbon chain length appears to be sharper than has been observed for a cloned rat odorant receptor, which shows a somewhat broad response profile for 7-, 8-, 9-, and 10-carbon n-aliphatic aldehydes (Zhao et al., 1997). Finally, the a-carboxylic acid moiety is critical for receptor binding, as agmatine and cadaverine (decarboxylated analogues of arginine and lysine, respectively) show essentially no binding to receptor 5.24 (Ki's>1 mM, or greater than 10,000 times the Kd for arginine or lysine). However, the interaction with the carboxylic acid is probably not dependent on the negative charge per se, since the carboxy-methylated arginine analogue, L-NAME, binds the receptor with modest affinity (Ki=1.0 mM).

The Goldfish Amino Acid Odorant Receptor Belongs to a Family of CaSR-Like Receptors. The sequence of the goldfish receptor 5.24 cDNA predicts a protein with seven membrane spanning regions preceded by a 566 amino acid N-terminal extracellular domain. Receptor 5.24 exhibits significant similarity to previously identified G protein-coupled receptors, including the CaSR (Hebert and Brown, 1995), the family of mGluR receptors (Tanabe et al., 1992), the family of vomeronasal V2R receptors (Herrada and Dulac, 1997; Matsunami and Buck, 1997; Ryba and Tirindelli, 1997), a family of olfactory CaSR- and V2R- related receptors found in the puffer fish, fugu (Naito et al., 1998) and goldfish (Cao et al., 1998), and two putative taste receptors found in the mouse (Hoon et al., 1999). Receptor 5.24 shares between 25 and 33% amino acid sequence identity with these receptors, showing a somewhat greater degree of similarity with human and fugu CaSR sequences. In spite of this weak homology to the CaSR and mGluR sequences, receptor 5.24 is not activated by calcium or glutamate.

The N-terminal extracellular domain of the mGluR is required for glutamate binding (O'Hara et al., 1993; Takahashi et al., 1993), and this region of the metabotropic as well as ionotropic glutamate receptors shows significant sequence similarity with bacterial periplasmic amino acid binding proteins (Nakanishi et al., 1990; O'Hara et al., 1993). Molecular modeling of the mGluR1 N-terminal domain based on the bacterial protein structures suggests that serine 165 and threonine 188 may interact with glutamate by coordination of the amino acid ligand's a-amino and a-carboxyl moieties; conservative mutations at these positions in mGluR1 results in a significant reduction in agonist binding (O'Hara et al., 1993). Interestingly, the corresponding two residues are conserved in receptor 5.24 (serine 152 and threonine 175), but not in the CaSR or in every V2R sequence. These residues in the goldfish receptor probably serve to coordinate the high affinity binding of amino acid odorants.

A Family of Olfactory CaSR-Like Receptors Related to the Goldfish Amino Acid Odorant Receptor. Recent work by others has identified members of a family of CaSR-like receptors that show similarity to receptor 5.24 and are specifically expressed in the goldfish olfactory epithelium (Cao et al., 1998). To identify additional receptor sequences in this gene family, we performed PCR on goldfish olfactory cDNA using degenerate primers based on motifs conserved among the N-terminal regions of receptor 5.24, CaSR, mGluR, and V2R sequences. Subcloning and DNA sequencing of the resulting PCR products revealed numerous CaSR-like sequences (SEQ ID NOS:3–6) that can be grouped into 5 distinct subfamilies. Within this portion of the N-terminal domain, the goldfish CaSR-like olfactory receptor subfamilies exhibit between 20 and 43% amino acid identity. Receptor 5.24 is the most divergent member of the group of receptors identified thus far, showing 20 to 27% similarity with the other sequences in this region. The receptor 5.24 full length cDNA detects 1–2 bands in genomic DNA blots, suggesting that this gene exists as a single copy in the goldfish genome.

In addition, full-length CaSR-like sequences are readily isolated from cDNA libraries using the foregoing techniques. For example, full, native length CaSR-like protein sequences SEQ ID NOS:7–8, 10 and 12 are encoded by full length goldfish cDNAs. Natural coding sequences for SEQ ID NOS:10 and 12 are shown as SEQ ID NOS:9 and 11, respectively. Furthermore, heterologous CaSR-like sequences are readily isolated using these techniques. For example, a zebrafish protein shown to be functionally and structurally similar to goldfish 5.24 (ca. 70% amino acid identity)is shown as SEQ ID NO:14 (the natural coding sequence is shown as SEQ ID NO:13).

Expression Patterns of Goldfish Olfactory CaSR-Like Receptors. Analysis of receptor 5.24 expression by RNA blots revealed that the mRNA encoding this receptor is expressed in olfactory epithelium but not in brain, kidney, liver, muscle, ovary, intestine, or testis. The receptor 5.24 probe also detects at high stringency an mRNA in skin from the trunk, gill, lips, tongue, and palatal organ. Similar RNA blot analysis with probes for receptor 5.3 and receptor 3.13 indicate that these genes are expressed exclusively in olfactory epithelium.

RNA in situ hybridizations were performed to determine the expression patterns of the goldfish olfactory CaSR-like sequences in the olfactory epithelium. We probed tissue sections with an 35S-labeled antisense RNA probe corresponding to the N-terminal extracellular domain of receptor 5.24. This is the most divergent region of this class of receptor, and therefore is expected to anneal only to receptor 5.24 under the stringent conditions of hybridization used in these experiments. We found receptor 5.24 mRNA expressed widely over the apical and medial portions of the olfactory sensory epithelium—regions which contain the olfactory sensory neurons. In situ hybridizations using a digoxigenin-labeled probe confirm that receptor 5.24 is expressed in a large fraction of cells in the neuronal layers of the sensory epithelium. These observations are consistent with electrophysiological recordings which suggest that roughly half of the olfactory neurons in fish can respond to amino acid stimuli (Kang and Caprio, 1995; Nevitt and Dittman, 1999). In situ hybridizations using a probe for receptor 5.3 indicate that this mRNA is also localized to a large subset of cells. In contrast to the broad patterns of receptor 5.24 and receptor 5.3 expression, other CaSR-like receptors are expressed in punctate patterns within the olfactory epithelium. Probes for receptor 3.13, receptor 9, and receptor 10 subfamily members hybridize to a small subset of cells (ca. 1–5% each).

We noticed that signal strengths for receptor 5.24 in situ hybridizations were consistently weaker than for the other receptors. This appears to be a peculiarity of the receptor 5.24 mRNA and not due to a low level of its expression, as screening of the goldfish olfactory cDNA library with olfactory CaSR-like sequences reveals that these RNAs are expressed at roughly equivalent levels (each sequence is represented at between 1 in ~100,000 clones [receptors 5.24 and 5.3] to 1 in 600,000 clones [receptor 10.8]).

Cells expressing the goldfish CaSR-like receptors localize more apically than we typically observe for olfactory neurons expressing the olfactory cyclic nucleotide-gated ion channel (Goulding et al., 1992; see below) or odorant receptors belonging to the family originally described by Buck and Axel (1991). The fish olfactory epithelium contains two major classes of sensory cells, the ciliated and microvillous neurons, that are segregated along the apical-basal axis (Yamamoto, 1982). The microvillous cells reside in the apical portion of the epithelium in a zone above and distinct from the ciliated neurons, whose cell bodies lie medially. Previous in situ hybridization studies have shown that the class of receptors originally described by Buck and Axel (1991), as well as the cyclic nucleotide-gated ion channel, are expressed in the medially-disposed ciliated olfactory neurons in fish (Goulding et al., 1992; Ngai et al., 1993a; Ngai et al., 1993b). Thus, the goldfish CaSR-like receptors are probably expressed in microvillous olfactory neurons (see also Cao et al., 1998).

Localization of Receptor 5.24 mRNA Expression in Non-Olfactory Tissue. The expression of receptor 5.24 mRNA in external epithelia raises the question as to whether this receptor might be playing a chemosensory function outside of the olfactory system. These epithelia contain both taste buds as well as solitary chemosensory cells; both of these systems are sensitive to amino acid stimuli in fish (Sorensen and Caprio, 1998), although facial nerve recordings in goldfish indicate that arginine is a poor taste stimulus in this species. We therefore performed additional in situ hybridizations to determine whether receptor 5.24 is indeed expressed in these chemosensory systems. Exemplary data showed representative tissue sections of gill rakers that were hybridized with a digoxigenin-labeled receptor 5.24 probe. The rakers are non-respiratory structures associated with the gill arches and are covered with an epithelium containing taste buds and solitary chemosensory cells. Examination of these tissue sections as well as numerous others similarly hybridized with the receptor probe indicates that this sequence is expressed widely in the overlying epithelium, but is distinctly excluded from taste buds. In addition, the epithelial cells expressing receptor 5.24 are far too numerous to be accounted for solely by the solitary chemosensory cells, which are relatively rare and dispersed in the epithelium (hence the term "solitary;" Sorensen and Caprio, 1998). Thus, these results argue against a role for receptor 5.24 —an odorant receptor tuned to recognize basic amino acids—in non-olfactory chemosensory transduction.

Experimental Procedures: Expression Cloning. Poly(A)+ RNA was prepared from adult male goldfish olfactory rosettes. cDNA was synthesized using an oligo(dT) primer and double stranded DNA was ligated directionally into pSPORT-1 plasmid (Life Technologies, Inc.) via 5' Sal I and 3' Not I restriction sites. Ligation reactions were introduced into E. coli by electroporation. Plasmid DNA was prepared from pools of 900–1000 clones, linearized with Not I, purified, and used as template for in vitro transcription with T7 RNA polymerase. For production of cRNAs encoding G protein and GIRK subunits, cDNAs for Gaolf (Jones and Reed, 1989) and the GIRK subunits Kir 3.1 (Reuveny et al., 1994) and Kir 3.4 (Ashford et al., 1994) were amplified by PCR using Pfu polymerase and subcloned into the RNA expression vector, pGEMHE (Liman et al., 1992). Following in vitro transcriptions, cRNAs were precipitated in LiCl and resuspended in water.

Oocytes were removed from anesthetized Xenopus laevis and treated with collagenase. Forty nanograms of cRNA from each cDNA library pool (~40 pg cRNA/clone) was injected per oocyte, together with cRNAs encoding Gaolf and the GIRK subunits Kir 3.1 and Kir 3.4 (~30 pg each). Approximately 30 pools were assayed before these primary screens were halted. Injected oocytes were incubated at 17° C. for over 80 hours prior to electrophysiological recordings. Recordings were performed by two-electrode voltage clamping using an Axoclamp-2A amplifier (Axon Instruments) or a Dagan CA-1 amplifier (Dagan Corp.). Data acquisition and analysis were performed using pCLAMP software (Axon Instruments). Membrane potential was held at −80 mV. For trials involving GIRK, oocytes were first perfused with Na-MBSH (88 mM NaCl, 1 mM KCl, 2.4 mM NaHCO3, 10 mM Hepes, pH 7.5, 0.82 mM MgSO4[7H2O], 0.33 mM Ca[NO3]2[4H2O], 0.41 mM CaCl2[2H2O]), and then switched into K-MBSH, which contains elevated K+ (88 mM KCl, 1 mM NaCl) until the basal current had stabilized (~45 seconds) before challenging with agonist. Recordings on oocytes injected with receptor 5.24 in the absence of Gaolf and/or GIRK subunits were performed in Na-MBSH. Oocytes were exposed to solutions containing different agonists by switching bathing solutions with an 8 channel valve (Hamilton).

DNA sequencing was carried out with a Pharmacia AlfExpress sequencer. Sequences were analyzed using Mac Vector software.

Mammalian Cell Culture and DNA Transfections. For cell transfections, the receptor 5.24 cDNA insert was subcloned into two expression vectors: CMVI, which utilizes a human cytomegalovirus (CMV) immediate early promoter-enhancer plus the CMV intron A sequence to drive expression, and 608RX-2.2L, which is similar to CMVI except the cDNA insert is followed by an internal ribosome entry site (IRES)—enhanced green fluorescent protein (EGFP) coding sequence; 608RX-2.2L also contains a puromycin resistance gene. For transient assays, HEK 293 cells expressing the SV40 large T antigen (293 TSA cells) were transfected with the CMVI-receptor 5.24 or CMVI control plasmid using lipofectamine (Life Technologies) and harvested at 48 hours for membrane preparations. For stable cell lines, 293-TSA cells were transfected with the 608RX-2.2L-receptor 5.24 plasmid or a control 608RX-2.2L plasmid and selected in puromycin. Colonies showing high levels of EGFP fluorescence (as judged by epifluorescence microscopy) were picked, expanded, and screened for 3H-L-arginine binding (see below). In five independent receptor 5.24-transfected stable cell lines, receptor densities (Rt) varied between 0.5 and 6.0 pmol L-arginine binding sites/ mg membrane protein. In four independent 608RX-2.2L-transfected control cell lines, EGFP expression was comparable to receptor 5.24-transfected cells, but L-arginine binding was indistinguishable from untransfected cells (Rt= 0.01–0.03 pmol/mg). All competition binding assays and signal transduction studies were performed using the stable cell line 5.24–20 (Rt=2.0 pmol /mg) and a control cell line (2.2-9) stably transfected with vector alone (Rt=0.03 pmol/ mg).

Membrane Preparations and Ligand Binding Assays. Membranes for ligand binding assays were prepared by washing confluent cells three times with phosphate buffered saline (PBS), detaching cells with a PBS-based enzyme-free dissociation solution, and resuspending cells in ice-cold 5.0 mM Hepes, pH 7.4, 1.0 mM EDTA, 1.0 $\mu$g/ml leupeptin, 0.5 mM PMSF. All subsequent manipulations were performed on ice. After a 30 min incubation, the cell suspension was homogenized and centrifuged at 100,000×g for 30 min. Cell membrane pellets were washed twice by resuspension and centrifugation in binding buffer (20 mM Hepes, pH 7.4, 1.0 mM EDTA, 2.0 mM MgCl2, 1.0 $\mu$g/ml leupeptin, 0.5 mM PMSF), resuspended in binding buffer, and frozen at −80° C.

Saturation binding assays were performed using 20–25 $\mu$g of membrane protein in a final volume of 100 $\mu$l binding buffer and increasing concentrations of [2,3-3H] L-arginine (specific activity=40 Ci/mmol; Dupont NEN). Non-specific binding was measured in the presence of 500 $\mu$M unlabeled L-arginine. Competition assays were performed with 500 nM [2,3-3H] L-arginine and increasing concentrations of competitor ligands. All incubations were performed at 4° C. for 60 min and terminated by rapid filtration through Whatman GF/C filters pretreated with ice cold 0.1% polyethyleneimine. Filters were washed three times with 4.0 ml ice cold 20 mM Hepes, pH 7.4, and retained radioactivity was measured by scintillation counting. All experiments were performed in triplicate and repeated at least twice. Data were analyzed by nonlinear curve fitting using Origin software (Microcal). The concentration of competitor which caused 50% inhibition of 3H-L-arginine binding (IC50) was determined by non-linear curve-fitting; inhibition constants were calculated according to the equation $K_i = (IC50)/(1+[3H\text{-}arginine]/K_d)$.

IP3 and cAMP Measurements. For measurements of IP3 and cAMP, cell lines 5.24-20 and 2.2-9 (negative control) were plated at densities of $3.5 \times 10^5$ cells/well in 24 well plates and incubated overnight in DMEM containing 10% FBS. All subsequent manipulations prior to reaction termination were performed at 37° C. in 5% CO2. Prior to odorant exposure, confluent cells were washed twice with PBS to remove free amino acids and incubated for 3 hours in amino acid-free media (Earle's Balance Salt Solution containing 0.1% BSA) to allow for recovery from potential desensitization of receptors or downstream signaling pathways. For IP3 assays, cells were washed once with PBS, pre-incubated for 15 min in PBS containing 10 mM LiCl, and then exposed to odorants in 400 μl PBS/10 mM LiCl for 30 min. IP3 levels were determined by a radioreceptor competition assay (Dupont NEN). For cAMP measurements, after the 3 hour amino acid-free preincubation cells were washed once with PBS, preincubated for 15 min in PBS containing 0.5 mM IBMX, and exposed to odorants in 400 μl PBS/0.5 mM IBMX for 30 min. cAMP levels were determined by radioimmunoassay (DuPont NEN).

PCR. PCR was performed to identify additional CaSR-like odorant receptor cDNAs. Three degenerate oligonucleotide primers were designed based on an alignment of receptor 5.24, mGluR (Duvoisin et al., 1995), human CaSR (Garrett et al., 1995), and mammalian V2R2 (Herrada and Dulac, 1997; Matsunami and Buck, 1997; Ryba and Tirindelli, 1997) sequences:

Primer A: corresponding to amino acids 211–215 in receptor 5.24;
Primer B: corresponding to amino acids 518–514 in receptor 5.24;
Primer C: corresponding to amino acids 755–751 in receptor 5.24.

Nested PCR was performed on plasmid library pools containing approximately 20,000 clones. DNA from each library pool was used as template for a primary PCR reaction using a 5' T7 primer with Primer C. Primary PCR reactions were separated on a 1% agarose gel and products between 1–4 kb were excised, eluted, and used as template for a secondary PCR reaction using Primer A and Primer B. Secondary PCR products were electrophoresed on a 1% agarose gel and fragments of ~1 kb were subcloned into the TA plasmid vector (Invitrogen) and sequenced.

RNA Blot Analysis and In Situ Hybridizations. The distribution of receptor 5.24 mRNA in goldfish tissues was determined by RNA blot analysis, using 32P-labeled antisense RNAs as probes at high stringency (Ambion). One-half microgram of poly(A)-enriched RNA from each goldfish tissue analyzed was electrophoresed under denaturing conditions, blotted to a nylon membrane, and probed with a 600 nt RNA probe corresponding to amino acids 389–600 of receptor 5.24. Since the full-length receptor 5.24 cDNA appears to recognize a single gene in genomic DNA blots, and sequences encoding this region comprise the most divergent portion of this class of receptors, this probe most likely is entirely specific for receptor 5.24 RNA under stringent hybridization conditions. As a control, the membrane was subsequently hybridized to a goldfish b-actin RNA probe.

RNA in situ hybridizations were performed on 20 mm-thick fresh frozen tissue sections from adult goldfish olfactory rosettes, essentially as described (Barth et al., 1996; Barth et al., 1997). Slides were hybridized with 35S-labeled (107 cpm/ml) or digoxigenin-labeled (1 mg/ml) probes at 60–65° C. for a minimum of 16 hours and washed in 0.2×SSC at 65° C. Slides hybridized with 35S probes were additionally treated with 20 mg/ml RNase A, rewashed in 0.2×SSC at 65° C., dehydrated, dipped in Kodak NTB-2 emulsion, exposed for 14–28 days at 4° C., developed, and counterstained with toluidine blue. Digoxigenin-labeled probes were visualized with an alkaline phosphatase-conjugated anti-digoxigenin antibody and chromogenic development in NBT/BCIP.

For receptor 5.24 localization, a ~1.8 kb Pst I fragment corresponding to the first 600 amino acids of the full-length receptor was subcloned into pBluescript and used for in vitro transcription of 35S- and digoxigenin labeled RNA probes. Digoxigenin-labeled probes for receptors 3.13 and 5.3 were synthesized from the cloned ~1 kb PCR inserts derived from these receptors' N-terminal domains. To identify members of the receptor family initially identified by Buck and Axel (1991), degenerate reverse transcription PCR was carried out on goldfish olfactory RNA, as described previously (Barth et al., 1996). One goldfish clone from this class of receptors, designated D1/113-6, was used to synthesize digoxigenin-labeled RNA probes. Cells expressing the olfactory cyclic nucleotide-gated channel were localized with a digoxigenin-labeled probe synthesized from a 2.5 kb full-length zebrafish cDNA (see Barth et al., 1996).

References:
Abe, K., et al. (1993). J. Biol. Chem. 268, 12,033–12,039.
Ashford, M. L., Bond, C. T., Blair, T. A., and Adelman, J. P. (1994). Nature 370, 456–459.
Barth, A. L., Dugas, J. C., and Ngai, J. (1997). Neuron 19, 359–369.
Barth, A. L., Justice, N. J., and Ngai, J. (1996). Neuron 16, 23–34.
Barth, A. L., Dugas, J. C., and Ngai, J. (1997). Neuron 19, 359–369.
Berghard, A., and Buck, L. B. (1996). J. Neurosci. 16, 909–918.
Berghard, A., Buck, L. B., and Liman, E. R. (1996). Proc. Natl. Acad. Sci. USA 93, 2365–2369.
Brunet, L. J., Gold, G. H., and Ngai, J. (1996). Neuron 17, 681–693.
Buck, L., and Axel, R. (1991). Cell 65, 175–187.
Buck, L. B. (1996). Ann. Rev. Neurosci. 19, 517–544.
Cagan, R. H., and Zeiger, W. N. (1978). Proc. Natl. Acad. Sci. USA 75, 4679–4683.

Cao, Y., Oh, B. C., and Stryer, L. (1998). Proc. Natl. Acad. Sci. USA 95, 11,987–11,992.
Caprio, J. (1978). J. Comp. Physiol. 123, 357–371.
Caprio, J., and Byrd, R. P. (1984). J. Gen. Physiol. 84, 403–422.
Collins, G. G. (1974). Brain Res. 76, 447–59.
Dreyer, W. J. (1998). Proc. Natl. Acad. Sci. USA 95, 9072–9077.
Dulac, C., and Axel, R. (1995). Cell 83, 195–206.
Duvoisin, R. M., Zhang, C., and Ramonell, K. (1995). J. Neurosci. 15, 3075–3083.
Friedrich, R. W., and Korsching, S. I. (1997). Neuron 18, 737–752.
Garrett, J. E., et al. (1995). J. Biol. Chem. 270, 12919–12925.
Goulding, E. H., et al. (1992). Neuron 8, 45–58.
Halpern, M. (1987). Annu. Rev. Neurosci. 10, 325–362.
Hara, T. J. (1994). Acta Physiol. Scand. 152, 207–217.
Hebert, S. C., and Brown, E. M. (1995). Curr. Opin. Cell Biol. 7, 484–492.
Herrada, G., and Dulac, C. (1997). Cell 90, 763–773.
Hoon, M. A., et al. (1999). Cell 96, 541–551.
Huque, T., and Bruch, R. C. (1986). Biochem. Biophys. Res. Comm. 137, 36–42.
Jia, C., and Halpern, M. (1996). Brain Res. 719, 117–128.
Jones, D. T., and Reed, R. R. (1989). Science 244, 790–795.
Kang, J., and Caprio, J. (1995).. J. Neurophysiol. 73, 172–177.
Krautwurst, D., Yau, K. W., and Reed, R. R. (1998). Cell 95, 917–926.
Lim, N. F., et al. (1995). J. Gen. Physiol. 105, 421–439.
Liman, E. R., Tytgat, J., and Hess, P. (1992). Neuron 9, 861–871.
Malnic, B., Hirono, J., Sato, T., and Buck, L. B. (1999) Cell 96, 713–723.
Margolis, F. L. (1974). Science 184, 909–911.
Masu, M., et al. (1991). Nature 349, 760–765.
Masu, Y., et al. (1987). Nature 329, 836–838.
Matsunami, H., and Buck, L. B. (1997). Cell 90, 775–784.
Medler, K. F., Hansen, A., and Bruch, R. C. (1998). Neuroreport 9, 4103–4107.
Michel, W. C., and Derbidge, D. S. (1997). Brain Res. 764, 179–87.
Michel, W. C., and Lubomudrov, L. M. (1995). J. Comp. Physiol. A 177, 191–199.
Naito, T., et al. (1998). Proc. Natl. Acad. Sci. USA 95, 5178–5181.
Nakanishi, N., Shneider, N. A., and Axel, R. (1990). Neuron 5, 569–581.
Nef, P., et al. (1992). Proc. Natl. Acad. Sci. USA 89, 8948–8952.
Nef, S., and Nef, P. (1997). Proc. Natl. Acad. Sci. USA 94, 4766–4771.
Nevitt, G., and Dittman, A. (1999). Integr. Biol. 1, in press.
Ngai, J., et al. (1993a). epithelium. Cell 72, 667–680.
Ngai, J., Dowling, M. M., Buck, L., Axel, R., and Chess, A. (1993b). Cell 72, 657–666.
Nicoll, R. A. (1971). Brain Res. 35, 137–49.
O'Hara, P. J., et al. (1993).. Neuron 11, 41–52.
Parmentier, M., et al. (1992). Nature 355, 453–455.
Ressler, K. J., Sullivan, S. L., and Buck, L. B. (1993). Cell 73, 597–609.
Restrepo, D., Boekhoff, I., and Breer, H. (1993). Amer. J. Physiol. 264, 906–911.
Reuveny, E., et al (1994). Nature 370, 143–146.
Ryba, N. J., and Tirindelli, R. (1997).. Neuron 19, 371–379.
Sengupta, P., Chou, J. C., and Bargmann, C. I. (1996). Cell 84, 899–909.
Sharon, D., Vorobiov, D., and Dascal, N. (1997). J. Gen. Physiol. 109, 477–490.
Shepherd, G. M. (1994). Neuron 13, 771–790.
Sorensen, P. W., and Caprio, J. C. (1998). Chemoreception. In The Physiology of Fishes, 2nd edition, D. H. Evans, ed. (Boca Raton: CRC Press), pp. 375–405.
Sorensen, P. W., et al. (1998). Curr. Opin. Neurobiol. 8, 458–467.
Sorensen, P. W., Hara, T. J., and Stacey, N. E. (1987). J. Comp. Physiol. A 160,305–313.
Sorensen, P. W., et al. (1988). Biol. Reprod. 39, 1039–1050.
Takahashi, K., et al. (1993). J. Biol. Chem. 268, 19,341–19, 345.
Tanabe, Y., Masu, M., Ishii, T., Shigemoto, R., and Nakanishi, S. (1992). Neuron 8, 169–79.
Yamamoto, M. (1982). In Chemoreception in Fishes, T. J. Hara, ed. (Amsterdam: Elsevier Scientific Publishing Company), pp. 39–59.
Zhang, Y., et al. (1997). Proc. Natl. Acad. Sci. USA 94, 12,162–12,167.
Zhao, H., et al. (1997). Science 279, 237–242.
Zhou, Q. Y., et al. (1990). Nature 347, 76–80.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting odorant receptor—ligand binding, said method comprising steps:
   a) recombinantly expressing or isolating an odorant receptor comprising a ligand binding domain of a polypeptide consisting of SEQ ID NO:2;
   b) incubating a mixture of the receptor and a ligand of the receptor; and
   c) detecting specific binding of the receptor and the ligand.

2. A method according to claim 1, wherein the receptor is SEQ ID NO:2.

3. A method according to claim 1, wherein the receptor is in a membrane.

4. A method according to claim 2, wherein the receptor is a membrane.

5. A method according to claim 1, wherein the receptor is in a membrane and the detecting step is effected by measuring ligand-binding mediated signal transduction through the receptor, across the membrane.

6. A method according to claim 2, wherein the receptor is in a membrane and the detecting step is effected by measuring ligand-binding mediated signal transduction through the receptor, across the membrane.

7. A method according to claim 1, wherein the receptor is in a membrane of a cell and the detecting step is effected by measuring ligand-binding mediated signal transduction through the receptor, across the membrane, wherein the signal transduction is measured inferentially by detecting a change in IP3 or cAMP in the cell.

8. A method according to claim 2, wherein the receptor is in a membrane of a cell and the detecting step is effected by measuring ligand-binding mediated signal transduction through the receptor, across the membrane, wherein the signal transduction is measured inferentially by detecting a change in IP3 or cAMP in the cell.

9. A method according to claim 1, wherein the detecting step is effected by a ligand displacement assay.

10. A method according to claim 2, wherein the detecting step is effected by a ligand displacement assay.

11. A method according to claim 5, wherein the detecting step is effected by a ligand displacement assay.

12. A method according to claim 6, wherein the detecting step is effected by a ligand displacement assay.

13. A method according to claim 1, wherein the mixture further comprises a candidate modulator of the specific binding of the receptor and the ligand.

14. A method according to claim 2, wherein the mixture further comprises a candidate modulator of the specific binding of the receptor and the ligand.

15. A method according to claim 5, wherein the mixture further comprises a candidate modulator of the specific binding of the receptor and the ligand.

16. A method according to claim 6, wherein the mixture further comprises a candidate modulator of the specific binding of the receptor and the ligand.

17. A method according to claim 7, wherein the mixture further comprises a candidate modulator of the specific binding of the receptor and the ligand.

18. A method according to claim 8, wherein the mixture further comprises a candidate modulator of the specific binding of the receptor and the ligand.

* * * * *